US012740736B2

(12) United States Patent
De Luca et al.

(10) Patent No.: US 12,740,736 B2
(45) Date of Patent: Sep. 22, 2026

(54) DETERMINING A BIOPOTENTIAL OF DEEP LAYER MUSCLES

(71) Applicant: Delsys Incorporated, Natick, MA (US)

(72) Inventors: Gianluca De Luca, Natick, MA (US); Joshua C Kline, Natick, MA (US)

(73) Assignee: Delsys Incorporated, Natick, MA (US)

( * ) Notice: Subject to any disclaimer, the term of this patent is extended or adjusted under 35 U.S.C. 154(b) by 424 days.

(21) Appl. No.: 18/496,024

(22) Filed: Oct. 27, 2023

(65) Prior Publication Data

US 2024/0050022 A1 Feb. 15, 2024

Related U.S. Application Data

(63) Continuation of application No. PCT/US2022/026642, filed on Apr. 28, 2022.

(Continued)

(51) Int. Cl.

*A61B 5/1455* (2006.01)

*A61B 5/00* (2006.01)

(Continued)

(52) U.S. Cl.

CPC .............. *A61B 5/274* (2021.01); *A61B 5/257* (2021.01); *A61B 5/296* (2021.01); *A61B 5/313* (2021.01);

(Continued)

(58) Field of Classification Search

CPC ................................ A61B 5/296; A61B 5/274

See application file for complete search history.

(56) References Cited

U.S. PATENT DOCUMENTS 6,415,170 B1 7/2002 Loutis et al.
8,303,982 B2 11/2012 Smith et al.

(Continued)

FOREIGN PATENT DOCUMENTS

WO WO 2012/034014 A2 3/2012
WO WO 2018/098417 A1 5/2018

OTHER PUBLICATIONS

European Search Report, Dated Aug. 7, 2024.

(Continued)

*Primary Examiner* — Marjan Fardanesh

(74) *Attorney, Agent, or Firm* — Westborough IP Group, LLC

(57) ABSTRACT

Determining a biopotential of deep layer muscles includes arranging electrodes on skin of a subject in a pattern corresponding to muscle tissue fibers of the subject, electrically coupling a subset of the electrodes to form a common reference node having a reference potential, and determining bipotential signal differences for separate electrodes that are not members of the first subset. For each of the separate electrodes, a biopotential difference is determined between a biopotential detected by each of the separate electrodes and the reference potential. An extent of the biopotential difference attributable to at least one deep-layer muscle is determined based on the biopotential differences. The pattern may be a two-dimensional array having columns of the electrodes arranged in a first dimension parallel with the muscle tissue fibers and a plurality of rows of the electrodes arranged in a second dimension that is orthogonal to the first dimension.

18 Claims, 17 Drawing Sheets

Related U.S. Application Data

(60) Provisional application No. 63/182,280, filed on Apr. 30, 2021.

(51) Int. Cl.
*A61B 5/257* (2021.01)
*A61B 5/274* (2021.01)
*A61B 5/296* (2021.01)
*A61B 5/313* (2021.01)
*A61B 5/389* (2021.01)
*A61B 5/397* (2021.01)

(52) U.S. Cl.
CPC .............. *A61B 5/389* (2021.01); *A61B 5/397* (2021.01); *A61B 5/6835* (2013.01); *A61B 2560/0406* (2013.01); *A61B 2560/0468* (2013.01); *A61B 2562/0215* (2017.08); *A61B 2562/046* (2013.01); *A61B 2562/14* (2013.01); *A61B 2562/164* (2013.01); *A61B 2562/182* (2013.01); *A61B 2562/187* (2013.01); *A61B 2562/227* (2013.01)

(56) References Cited

U.S. PATENT DOCUMENTS

| | | | | |
|---|---|---|---|---|
| 8,449,469 | B2 | 5/2013 | Banet et al. | |
| 9,351,660 | B2 | 5/2016 | Gilmore et al. | |
| 10,004,420 | B2 | 6/2018 | Fadem | |
| 10,517,500 | B2 | 12/2019 | Kumar et al. | |
| 2012/0172682 | A1* | 7/2012 | Linderman ............ | A61B 5/389 600/300 |
| 2013/0041235 | A1 | 2/2013 | Rogers et al. | |
| 2014/0088377 | A1 | 3/2014 | Manzke et al. | |
| 2018/0184938 | A1* | 7/2018 | Davie .................. | A61B 5/6823 |
| 2019/0082996 | A1 | 3/2019 | Ang et al. | |
| 2020/0092988 | A1 | 3/2020 | Moczygemba | |

OTHER PUBLICATIONS

International Preliminary Report on Patentability for PCT Application No. PCT/US2022/026642, Dated Nov. 9, 2023.

International Search Report for PCT Application No. PCT/US2022/026642, Dated Sep. 9, 2022.

European Office Action, dated Mar. 12, 2026.

Sun Ye et al.: "Capacitive Biopotential Measurement for Electrophysiological Signal Acquisition: a Review", IEEE Sensors Journal, IEEE, vol. 16, No. 9, May 1, 2016 (May 1, 2016), pp. 2832-2853, XP011603334, ISSN: 1530-437X, DOI: 10.1109/JSEN.2016.2519392 [retrieved on Mar. 16, 2016].

Li Xian et al: "Design and evaluation of a non-contact wireless biopotential monitoring system with motion artifacts", 2017 IEEE EMBS International Conference on Biomedical & Health Informatics (BHI), IEEE, Feb. 16, 2017 (Feb. 16, 2017), pp. 69-72, XP033084864, DOI: 10.1109/BHI.2017.7897207 [retrieved on Apr. 11, 2017].

* cited by examiner 812a
803c
810
812b
803b
803a
A
800

804a
806a
803c
802
803b
803a
A
800
804b
806b 812b
810
804b
806b
802
800

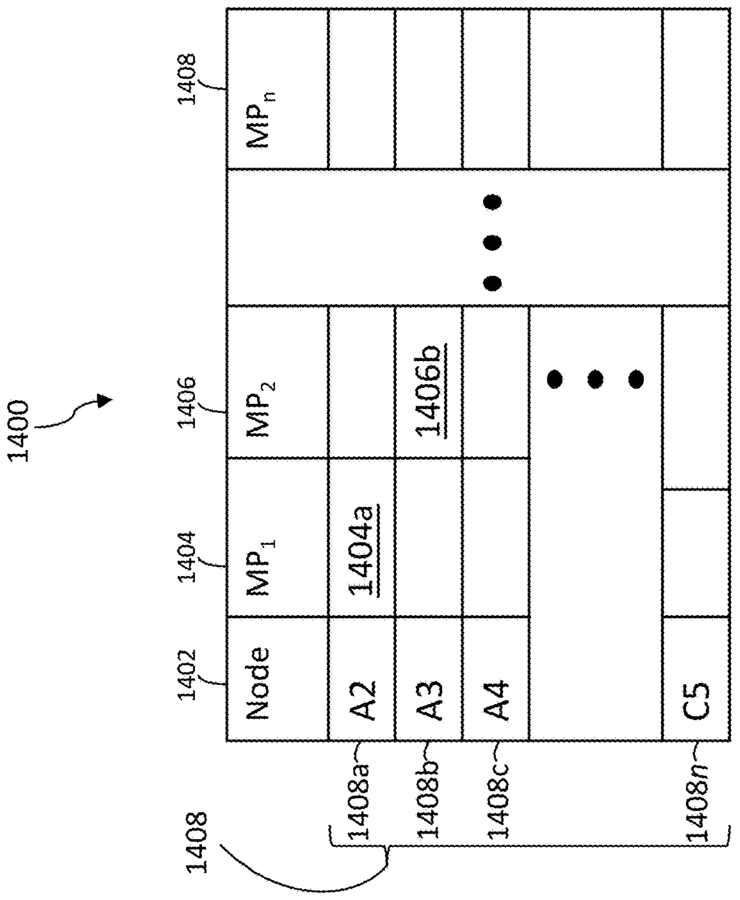

FIG. 14

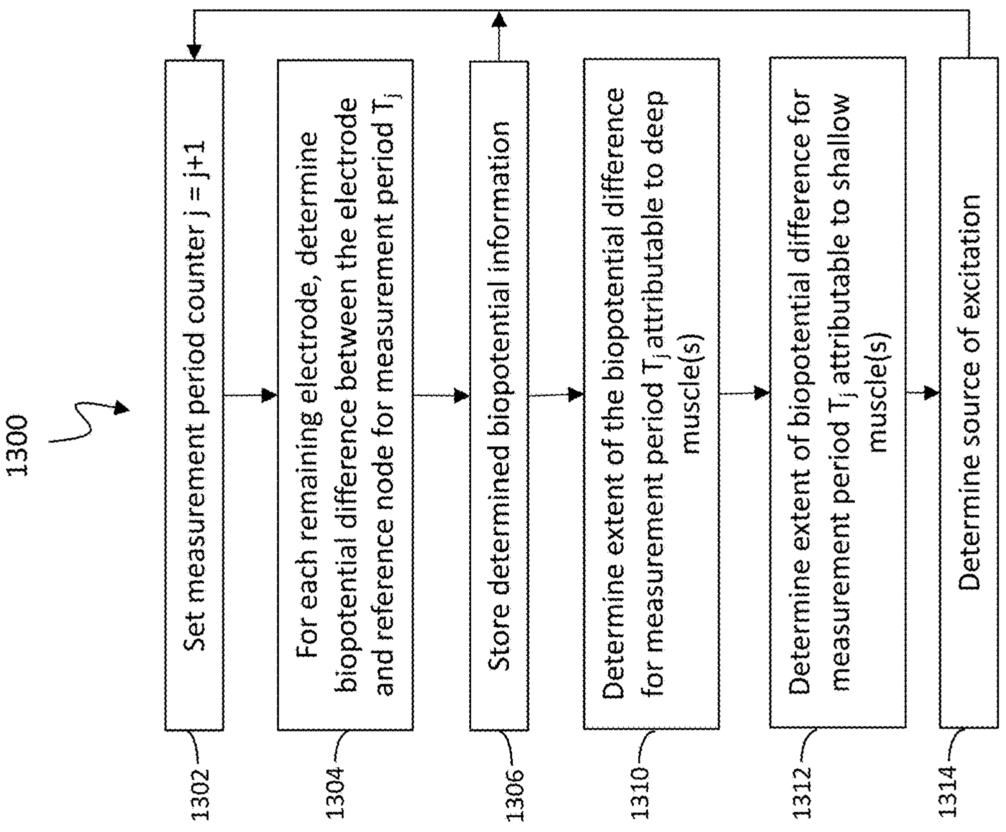

FIG. 13

1300
1302
Set measurement period counter j = j+1
1304
For each remaining electrode, determine biopotential difference between the electrode and reference node for measurement period $T_j$
1306
Store determined biopotential information
1310
Determine extent of the biopotential difference for measurement period $T_j$ attributable to deep muscle(s)
1312
Determine extent of biopotential difference for measurement period $T_j$ attributable to shallow muscle(s)
1314
Determine source of excitation
1400
1408
1402
1404
1406
1408
Node
$MP_1$
$MP_2$
$MP_n$
1408a
A2
1404a
1408b
A3
1406b
1408c
A4
1408n
C5

DETERMINING A BIOPOTENTIAL OF DEEP LAYER MUSCLES

BACKGROUND

Technical Field

This application relates to a medical device, and more particularly to a device for detecting and processing biopotential signals, and methods of making and using such a device and parts thereof.

Description of Related Art

Electromyography (EMG) involves evaluating the condition of muscles and the nerve cells, for example, motor neurons, that control them. EMG may involve the detection of biopotential signals from muscle tissue, triggered by electrical signals generated by motor neurons connected to the muscle tissue. Biopotentials are electrical signals (voltages) that are generated by physiological processes occurring within the body, specifically, the electrochemical activity of certain cells.

Currently accepted surface EMG technology limits the detection of muscle activity to superficial muscles (i.e., shallow muscles close to sensors on the skin), and may be hampered by poor signal quality, poor specificity of information, and an intrinsic inability to separate signal information generated form overlapping sources, including signal information generated from deep muscles vs. shallow muscles.

SUMMARY OF THE INVENTION

According to the system described herein, a skin interface includes a substrate having a first side facing a surface of a skin of a subject and a second side facing a surface of a device with a plurality of electrodes arranged in a pattern that detects and processes biopotential signals from the subject, the substrate having a plurality of openings that align with the plurality of electrodes, a first adhesive layer that adheres to the first side of the substrate and to the skin having a plurality of openings that align with the plurality of electrodes, and a second adhesive layer on the second side of the substrate that adheres to the surface of the device having a plurality of openings that align with the plurality of electrodes. The device may include a plurality of electrode structures, each electrode structure including one of the plurality of electrodes carried by a non-conductive carrier The second adhesive layer may include an adhesive optimized for adhesion to the conductive carriers of the electrode structures. The device may include a flexible encapsulant that encapsulates the plurality of electrode structures. The device may be constructed from materials that match stretch characteristics of the flexible encapsulant. The substrate may be made of a silicone-based polymer. The first adhesive layer may be pressure sensitive. The first adhesive layer may include an adhesive optimized for adhesion to the skin. The skin interface may also include an alignment layer on the second side of the substrate having interior sidewalls that conforms to at least a portion of an exterior side perimeter of the device to assist in aligning the plurality of openings with the plurality of electrodes. The alignment layer may be provided in a plurality of separate portions. The alignment layer may be made of foam. The skin interface may also include a tabular portion affixed to the substrate, the first adhesive layer and/orw2™ the second adhesive layer, the tabular portion being grippable by a human hand and of sufficient structural integrity to remain affixed to one or more of the substrate, the first adhesive layer and the second adhesive layer when pulled in a direction away from the skin with sufficient force to remove the article from the skin. The skin interface may be part of a system for detecting and processing biopotential signals. A system for detecting and processing biopotential signals may include the skin interface.

According further to the system described herein, determining a biopotential of deep layer muscles includes arranging a plurality of electrodes on skin of a subject in a pattern corresponding to muscle tissue fibers of the subject, electrically coupling a first subset of the plurality of electrodes to form a common reference node having a reference potential, determining a plurality of bipotential signal differences for first electrodes of the plurality of electrodes that are not members of the first subset, including, for each of the plurality of first electrodes, determining a biopotential difference between a biopotential detected by the first electrode and the reference potential, and, for each of the first electrodes, determining an extent of the biopotential difference attributable to at least one deep-layer muscle based on the plurality of biopotential differences. Determining a biopotential of deep layer muscles may also include electrically coupling a second subset of the plurality of electrodes to form a global common mode potential that provides common mode noise mitigation, where the second subset of the plurality of electrodes is separate from the first subset of the plurality of electrodes and separate from the first electrodes. The pattern may be a two-dimensional array having a plurality of columns of the electrodes arranged in a first dimension parallel with the muscle tissue fibers and a plurality of rows of the electrodes arranged in a second dimension orthogonal to the first dimension. The first subset of electrodes may be one of the plurality of rows of electrodes. Determining a biopotential of deep layer muscles may also include storing in a first data structure, for each of the plurality of first electrodes, a value indicative of the extent of the biopotential difference attributable to the at least one deep-layer muscle. Determining the plurality of biopotential signal differences for the first electrodes may include, for each of the plurality of first electrodes, determining a first biopotential difference between a first biopotential detected by the first electrode for a first period time and a first reference potential detected by the common reference node for the first period time and determining a second biopotential difference between a second biopotential detected by the first electrode for a second period time and a second reference potential detected by the common reference node for the second period time. Determining the extent of the biopotential difference attributable to at least one deep-layer muscle for each of the plurality of first electrodes may include determining a difference between the first biopotential difference determined for the first electrode and the second biopotential difference determined for another of the first electrodes that is adjacent to the first electrode relative to other ones of the first electrodes. Determining a biopotential of deep layer muscles may also include, for each of the plurality of first electrodes, determining an extent of the biopotential difference attributable to at least one shallow-layer muscle based on the plurality of biopotential differences. Determining a biopotential of deep layer muscles may also include storing in a first data structure, for each of the plurality of first electrodes, a first value indicative of the extent of the biopotential difference attributable to the at least one deep-layer muscle and a second value indicative of the extent of the biopotential difference attributable to the at least one shallow-layer muscle. Determining the extent of the biopotential difference attributable to at least one shallow-layer muscle may include, for at least one of the plurality of first electrodes, determining a first difference between a first of the plurality of biopotential differences determined for the first electrode and a second of the plurality of biopotential differences determined for a second electrode adjacent to the first electrode on a first side of the first electrode, determining a second difference between the first biopotential difference and a third of the plurality of biopotential differences determined for a third electrode adjacent to the first electrode relative to other first electrodes on a second side of the first electrode opposite the first side, and determining a third difference between the first difference and the second difference, where the third difference correlates to the extent of the biopotential difference attributable to at least one shallow-layer muscle for the at least one of the plurality of first electrodes. Determining the reference potential and determining the biopotential difference for each of the first electrodes may include using differential amplifier circuitry. The biopotential signals may be triggered by motoneurons. A device may perform at least some of the steps set forth above for determining a biopotential of deep layer muscles. The device may be part of a system for detecting and processing biopotential signals. A system for detecting and processing biopotential signals may include the device that performs at least some of the steps set forth above for determining a biopotential of deep layer muscles. A non-transitory computer readable medium may contain software that, when executed by a processor, perform at least some of the steps set forth above for determining a biopotential of deep layer muscles.

According further to the system described herein, an interconnection mechanism includes a plurality interconnected rigid or semi-rigid arms that are interconnected at midsections thereof and a plurality of attachment points formed by interconnections at ends of the arms that act as bearings to allow the arms to deform about the attachment points. The arms may freely rotate about the attachment points. The interconnection mechanism may also include a plurality of printed circuit boards coupled to the arms. At least a subset of the plurality of printed circuit boards may provide a distributed computational system. The distributed computational system may use electrical communication paths for communication between the plurality of printed circuit boards. The printed circuit boards may process electrical information detected by a plurality of electrodes coupled to the interconnection mechanism. The plurality of attachment points may be arranged in a two dimensional array that includes a plurality of rows having a first direction and a plurality of columns having a second direction and the electrical interconnection mechanism may resist deformation in the first direction and in the second direction. The arms are made of plastic or stiff silicone. The interconnection mechanism may be part of a system for detecting and processing biopotential signals. A system for detecting and processing biopotential signals may include the interconnection mechanism.

According further to the system described herein, a biopotential signal acquisition device includes a plurality of electrodes, an electro-mechanical structure having a plurality of conductive contacts affixed to the plurality of electrodes, one or more electronic components, and a plurality of connectors that mechanically and electrically couple the plurality of conductive contacts and the one or more electronic components, and a mesh fabric overlaying and bearing mechanical strain of the electro-mechanical structure. The mesh fabric may include a plurality of fibrous threads arranged as a grid in which a first subset of the plurality of threads align in a first direction and a second subset of the plurality of threads align in a second direction orthogonal to the first direction. The plurality of conductive contacts may be arranged in at least one row along a third direction that is oblique to the first direction and the second direction. The plurality of conductive contacts may be arranged in a two dimensional array that includes a plurality of rows and a plurality of columns, where the plurality of rows are aligned in a third direction that is oblique to the first direction and the second direction and the plurality of columns are aligned in a fourth direction oblique to the first direction and the second direction. The mesh fabric may be elastically deformable to enable the mesh fabric to conform to a non-uniform surface. The mesh fabric may dissipate static electrical charge. The mesh fabric may include a plurality of conductive threads. The conductive threads may have a non-conducting core coated with a conductive material. The mesh fabric may be electrically connected to a fixed electric potential provided by the electro-mechanical structure. The biopotential signals may be triggered by motor neurons. The biopotential signal acquisition device may be part of a system for detecting and processing biopotential signals. A system for detecting and processing biopotential signals may include the biopotential signal acquisition device.

According further to the system described herein, assembling a device that detects and processes biopotential signals includes arranging a plurality of electrode structures within a first mold, each electrode structure including an electrode carried by a non-conductive carrier, performing a first encapsulation including encapsulating the plurality of electrode structures with a first flexible encapsulant using a first molding process to produce a bottom part of the device, positioning an electromechanical construct that processes biopotential signals above the bottom part of the device, electrically coupling the electromechanical construct to the plurality of electrode structures, positioning the electromechanical construct within a second mold while the electromechanical construct is electrically coupled to the plurality of electrode structures, performing a second encapsulation including encapsulating the electromechanical construct with a second flexible encapsulant using a second molding process to produce a top part of the device, and bonding the top part to the bottom part to produce the device. Bonding the top part to the bottom part may be performed as part of the second molding process. Arranging the plurality of electrode structures may include arranging the plurality of electrode structures in a two-dimensional array. For each of the plurality of electrode structures, a top end of the electrode may not be enclosed by the non-conductive carrier and may extend beyond a top end of the non-conductive carrier. Performing the first encapsulation may result in the top end of the electrode structure being left exposed and may result in the top end of the electrode of the electrode structure extending beyond a top surface of the bottom part of the device. The electromechanical construct may include a plurality of conductive contacts, a plurality of electronic components and a plurality of connectors connecting the plurality of conductive contacts and the plurality of electronic components, and electrically coupling the electromechanical construct to the plurality of electrode structures may include electrically coupling the plurality of conductive contacts to the top ends of the electrodes of the electrode structures. Assembling a device that detects and processes biopotential signals may also include forming the plurality of electrode structures including, for each of a plurality of electrodes, encasing the electrode in the non-conductive carrier, wherein encasing the electrode results in the electrode being fully encased by the non-conductive carrier except for a bottom end of the electrode and the top end of the electrode. For each of the plurality of electrode structures, a bottom end of the electrode may not be enclosed by the non-conductive carrier and may extend beyond a bottom end of the non-conductive carrier. A bottom surface of the device may be formed from a bottom surface of the first flexible encapsulant and a bottom surface of each of the plurality of electrode structures. The bottom surface of each electrode structure may include a bottom surface of the non-conductive carrier and a bottom surface of the electrode, and the bottom surface of the electrode may protrude beyond a plane formed by the bottom surface of the non-conductive carrier and the bottom surface of the first flexible encapsulant. Assembling a device that detects and processes biopotential signals may also include, prior to encapsulating the electromechanical construct, overlaying the electromechanical construct with a mesh fabric that bears mechanical strain of the electromechanical construct, wherein performing the second encapsulation includes encapsulating the mesh fabric along with the electromechanical construct. The first flexible encapsulant and the second flexible encapsulant may be made of a same material or a same combination of materials. The first flexible encapsulant and the second flexible encapsulant may provide a hermetic and waterproof seal of the electromechanical construct. The biopotential signals may be triggered by motor neurons. The device that detects and processes biopotential signals may be assembled as set forth above and may be part of a system for detecting and processing biopotential signals and a system the detects and processes biopotential signals may include the device.

According further to the system described herein, an electrical circuit includes a first input electrically coupled to a first electrode in contact with skin of a subject and carrying a first biopotential signal detected at the first electrode, a second input electrically carrying a first reference signal, first differential amplifier circuitry including a first amplifier input that receives a first amplifier input signal, a second amplifier input that receives a second amplifier input signal, a first amplifier output and a second amplifier output, where the first differential amplifier circuitry generates a first amplifier output signal on the first amplifier output and a second amplifier output signal on the first amplifier output, and where a difference between the first amplifier output signal and the second amplifier output signal represents an amplified difference between the first amplifier input signal and the second amplifier input signal, and switching circuitry that selects connecting the first input to the first amplifier input or the second amplifier input and selects whether to connect the first reference signal to the first amplifier input. The electrical circuit may also include analog-to-digital converter circuitry electrically coupled to receive the first amplifier output signal and the second amplifier output signal, where the analog-to-digital converter circuitry samples the first amplifier output signal and the second amplifier output signal at a predefined rate and converts a difference between the first amplifier output and the second amplifier output from an analog signal to a digital signal. The digital signal may be a 24-bit digital signal. The first differential amplifier circuitry may include one or more impedance elements that are tuned to amplify the first amplifier input signal if the first amplifier input signal oscillates at a frequency within a predefined range, and amplify the second amplifier input signal if the second amplifier input signal oscillates at a frequency within the predefined range. The predefined range may be 10 Hertz-500 Hertz. The electrical circuit may also include a common node resistively coupled to the first amplifier output and the second amplifier output, wherein the common node carries a common mode potential and second differential amplifier circuitry having a first input to receive the common mode potential and a second input to receive a static reference signal of the electrical circuit, where the second differential amplifier circuitry produces as an output a noise cancellation signal. The first reference signal may be the static reference signal. The electrical circuit may include a third input electrically coupled to carry the noise cancellation signal. The switching circuitry may select whether to connect the first reference signal carried on the second input or the noise cancellation signal carried on the third input to the first amplifier input. The electrical circuit may detect and process biopotential signals. The first differential amplifier circuitry and the switching circuitry may be part of a first circuit block of the circuit corresponding to the first electrode. The electrical circuit may also include a plurality of additional electrodes in contact with the skin of the subject. The first biopotential signal may be triggered by motor neurons. A controller may control a rate at which the electric circuit samples biopotential signals from the first electrode. The electrical circuit may be part of a system for detecting and processing biopotential signals. A system for detecting and processing biopotential signals may include the electrical circuit.

According further to the system described herein, an electrical interconnection mechanism includes a plurality of electrically interconnected islands, a plurality of printed circuit boards electrically connected to and disposed on each of the islands, a plurality of conductive contacts electrically connected to at least one of the islands, and a plurality of elastically deformable conductive connectors that mechanically and electrically interconnect the islands and the contacts. The conductive connectors may be aligned along a dimension parallel to a dominant plane of the printed circuit boards. The conductive connectors may be elastically deformable in a plurality of dimensions to enable the conductive contact and the printed circuit boards to conform to a non-uniform surface. Each of the conductive connectors may have a serpentine shape. At least a subset of the plurality of printed circuit boards may provide a distributed computational system. The distributed computational system may use the plurality of elastically deformable conductive connectors for communication between the plurality of printed circuit boards. The conductive connectors may be stretchable to provide an increase in distance between the conductive contacts and the printed circuit boards. The printed circuit boards may process electrical information detected by a plurality of electrodes electrically connected to the plurality of contacts. The electrical interconnection mechanism may be part of a system for detecting and processing biopotential signals. A system for detecting and processing biopotential signals may includes the electrical interconnection mechanism.

According further to the system described herein, a carrier for an electrode includes a first cylindrical portion having a first solid annular portion and a first hollow cylindrical region radially inside of the first solid annular portion, a second cylindrical portion having a second solid annular portion and a second hollow cylindrical region radially inside of the second solid annular portion, the second hollow cylindrical region having a diameter that is less than a diameter of the first hollow cylindrical region, and an inset cylindrical portion coupled to and interposed between the first cylindrical portion and the second cylindrical portion and having an inset solid annular portion and a third hollow cylindrical region radially inside of the inset solid annular portion and having an outer diameter that is less than an outer diameter of the first cylindrical portion and less than an outer diameter of the second cylindrical portion. The first solid annular portion and the second solid annular portion may have a same outer diameter. The third hollow region and the second hollow region may have a same diameter. An outer surface of the first solid annular portion may be opposite to the inset cylindrical portion and is smooth and rigid. The outer surface of the first solid annular portion may be adherable to medical-grade adhesive tape. The carrier may receive an electrode having a cylindrical portion that provides a conductive contact to an electronic circuit and the second hollow region may fit around the cylindrical portion of the electrode. The electrode may have a flange with a diameter greater than a diameter of the cylindrical portion and the first hollow region may fit around the flange. The electrode may have a protruding portion projecting from the flange and a surface of the first annular portion may align with a portion of the flange to cause the protruding portion to protrude from the carrier. A portion of the electrode may extend from the second cylindrical portion of the carrier. At least one of the first cylindrical portion, the second cylindrical portion, and the inset cylindrical portion may be made of plastic. An exterior surface of the carrier may have at least one perforation. The carrier for an electrode may be part of a system for detecting and processing biopotential signals. A system for detecting and processing biopotential signals may include the carrier for an electrode.

According further to the system described herein, an electrode includes a cylindrical portion having a surfaced that provides a conductive contact to a circuit, an inset ring portion coupled to the cylindrical portion and having a diameter less than a diameter of the cylindrical portion, a flange portion coupled to the inset ring portion and having a diameter greater than the diameter of the cylindrical portion, and a protruding portion coupled to the flange portion and having a protruding side that provides a contact surface for the electrode. The inset ring may provide an interface joint with material for a carrier of the electrode. The protruding portion may have a semispherical shape. A surface of the protruding portion may be smooth. The electrode may be made of silver. A surface of the protruding portion may have a cavity extending into the protruding portion. The cavity may accept an ionic gel. The cylindrical portion may include a chamfered top edge. The chamfered edge may provide self-alignment when the electrode is coupled to an electrical contact. The electrode may be soldered to the electrical contact. The electrode is coupled to an electrode carrier having an axial cavity to receive the electrode. The electrode carrier may be cylindrical and the flange may provide a seal around the electrode to inhibit an ingress of moisture. The flange may have a diameter greater than a diameter of the protruding portion. The electrode may be part of a system for detecting and processing biopotential signals. A system for detecting and processing biopotential signals may include the electrode described above.

BRIEF DESCRIPTION OF THE DRAWINGS

Features and advantages of the present invention will become more apparent from the following detailed description of illustrative embodiments thereof taken in conjunction with the accompanying drawings in which:

FIG. 13 is a flowchart of a method of processing and analyzing biopotential information collected from a subject, according to an embodiment of the system described herein;

FIG. 14 is block diagram illustrating a data structure for storing biopotential information, according to embodiments of the system described herein.

DETAILED DESCRIPTION OF EMBODIMENTS

Figure 2A:
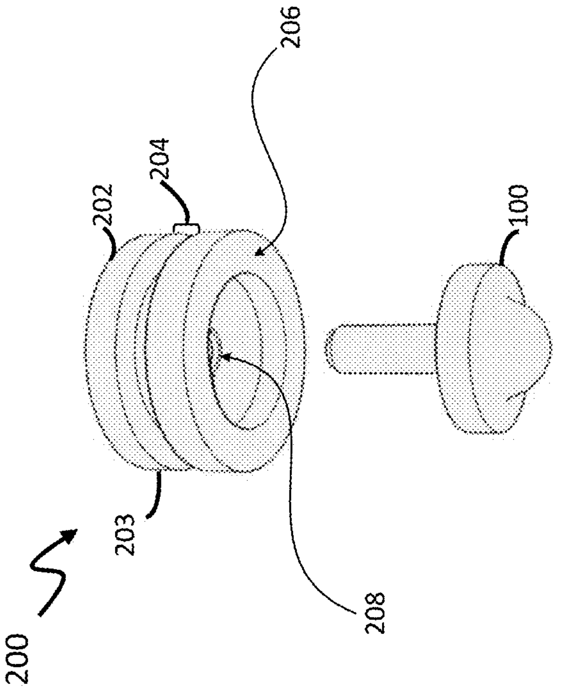
FIG. 2A is an exploded view of an electrode structure according to an embodiment of the system described herein.

Described herein is a system for detecting and processing biopotential signals, and methods of making and using such a system and parts thereof. The system may detect biopotentials from multiple locations concurrently. In some embodiments, the system may be configured to be flexible and to contact (e.g., adhere) temporarily to the skin of a subject (e.g., a human or animal). The system may be configured to implement one or more aspects of EMG, including detecting biopotential signals from muscle tissue resulting from muscle contraction, where such muscle contractions result from electrical signals triggered by motor neurons. The system may include a plurality of electrodes to detect biopotential signals, where the electrodes may be arranged in a pattern, for example, a two-dimensional array, and contacted to the skin of the subject so that the pattern of the electrodes generally aligns with one or more biological parts or areas of interest, for example, the muscle fibers of one or more muscles.

The electrodes may be electrically coupled to electrical contacts of a flexible electromechanical construct (FEC). The FEC may include the contacts, one or more islands and a plurality of connectors that electrically and mechanically couple components (e.g., printed circuit boards (PCBs)) on the islands to the contacts. The islands of the FEC may be configured with one or more electrical coupling paths that enable electrical coupling between electronic components (e.g., PCBs) on the islands to other PCBs and/or electrodes connected to the contacts of the FEC one or more. As used herein, an FEC with one or more electronic components electrically coupled to the islands of the FEC may be referred to as a "configured FEC." The connectors may enable the FEC to conform to a non-uniform surface, for example, the skin of a subject over a muscle group. The one or more components on the islands (e.g., PCBs) may be configured with hardware, firmware and/or software to determine and process biopotential information, for example, as part of implementing one or more aspects of EMG. In some embodiments, two or more PCBs of an FEC may be configured to work collaboratively, for example, to perform distributed processing of biopotential information.

The PCB(s) may be, or may include, one or more of: an application-specific integrated circuit (ASIC), a system on chip (SoC), a field programmable gate array (FPGA), another type of programmable logic, another type of circuit or chip, or any suitable combination of the foregoing. The PCB(s) may include analog circuitry for determining values of biopotentials detected by electrodes, including, for example, operational amplifiers (e.g., differential amplifiers), resistive circuitry, capacitive circuitry, impedance circuitry, inductive circuitry, other components, or any suitable combination of the foregoing, as described in more detail elsewhere herein. The PCB(s) also may include other circuitry, which may be programmed electrically and/or with software, including, for example, analog-to-digital converter (ADC) circuitry, digital signal processing (DSP) circuitry, power management circuitry, communication interfaces, transceivers, other circuitry, or any suitable combination of the foregoing, as described in more detail elsewhere herein.

The electrodes themselves may have a generally cylindrical shape, with one end of the electrode including a protruding portion ("protrusion") configured to depress into skin when applied as part of the system described herein, thereby providing a reliable physical and electrical contact with the skin of a subject. The other end (which may be referred to herein as the "top end") of the electrode may be configured to electrically couple to an external contact, for example, a contact of an FEC as described herein. The electrode may be manufactured from essentially pure silver (e.g., 99.9% pure) in order to provide a stable skin-electrode interface. Silver has desirable qualities which should minimize skin potential offset errors, and should minimize noise artifacts during movement. Other metals, metal alloys or other conductive materials that have desirable qualities that minimize skin potential offset errors and minimize noise artifacts during movement, other than silver, may be used.

Whereas known electrodes for detecting biopotentials may use silver-silver-chloride coatings and electrolytic gels or pastes to facilitate bipotential detection, an electrode according to an embodiment of the system described herein may not use such gels and coatings, and thus be considered a "dry" electrode. That is, rather than or in addition to using such coatings, gels and/or pastes, the electrode may consist essentially of silver and rely on natural occurring ions in the skin of the subject as well as skin moisture and/or sweat to facilitate biopotential detection. As described in more detail elsewhere herein, in some embodiments, the system may be configured to adhere to the skin of a subject. In such embodiments, the system may be configured to trap skin moisture around the protrusion of the electrode to facilitate ionic exchange with the electrode. Embodiments of an electrode according to the system described herein are described in more detail elsewhere herein.

Each electrode may be configured to be carried by a non-conductive (e.g., plastic or other polymer) electrode carrier such that the electrode is fully encased by (i.e., fits relatively snugly in) the electrode carrier except for the protrusion and the top end of the electrode. The electrode carrier may provide a seal around the electrode to prevent the influx of moisture to the electrode or at least a portion thereof, and may provide an interface between the electrode and an encapsulant. A bottom end of the electrode carrier may have a smooth, clean and rigid surface that can serve as a surface that adheres to medical grade tape or other adhesives of a skin interface that adheres a system as described herein to skin. This surface of the electrode carrier may serve in place of another material (e.g., silicone of an encapsulant as described herein) to provide better adhesion to the skin interface than the other material. A structure consisting of an electrode carried (e.g., encased as described herein) by an electrode carrier may be referred to herein as an "electrode structure." Embodiments of electrode structures and electrode carriers are described in more detail elsewhere herein.

In some embodiments of the system described herein, an electrical circuit for determining a biopotential may be provided, for example, as part of a device (e.g., a configured FEC thereof) as described elsewhere herein. The electrical circuit may include a plurality of circuit blocks, each circuit block corresponding (e.g., dedicated) to an electrode. Each circuit block may include switching circuitry to select between one or more reference potential signals and/or a biopotential signal detected from the electrode corresponding to the circuit block. The switching circuitry may feed the selected input signals as inputs to differential amplifier circuitry of the circuit block that generates an output representing a difference (amplified according to a gain of the amplifier circuitry) between the selected input signals. Each circuit block may include ADC circuitry to sample the output of the differential amplifier circuitry at a predefined rate.

An electronic system for detecting and processing biopotential signals that includes the electrical circuit also may include other components, for example, a microcontroller and a DSP, where the DSP logic may be implemented in hardware, software or firmware, or any suitable combination thereof. In some embodiments, the circuit blocks described elsewhere herein, microcontroller and the DSP are implemented on one or more PCBs residing on islands of an FEC as described herein. The microcontroller and/or DSP may be configured to control the rate at which samples are taken (e.g., 1000-20,000 times per second) and to process the signals. As the signals generated within the subject are sinusoids, and the detected biopotentials may be a combination of sinusoids, processing the signals may include determining root-mean-square (RMS) values from the sampled outputs, where the RMS values serve as the determined biopotential value for an electrode for a given period of time.

Empirical data has shown that a vast majority of the bioelectric signal emanating onto the skin surface from muscle cells includes energy in the spectrum of 10 Hz-500 Hz. Accordingly, the DSP may employ signal conditioning that results in a target bandpass of 10 Hz-500 Hz, may apply a digital filter that targets a maximally flat pass band area (e.g., <0.5 dB variation) to preserve biopotential amplitude information, and may use linear phase response to preserve biopotential temporal information. In some embodiments, the ADC circuitry may produce a highly granular digital value (e.g., 24 bits), which may reduce processing resources required (e.g., by the DSP) to condition the sampled signals. Embodiments of electrical circuits and other processing logic are described in more detail elsewhere herein.

In some embodiments, a mesh fabric may overlay a configured FEC, for example, on a top side of the configured FEC that is opposite a bottom side of the configured FEC that is (or is expected to be) electrically coupled to the electrodes. The mesh fabric may include fibrous threads that may be natively conducting (e.g., metal wire) or made of non-conductive material coated with a conductive finish. The mesh fabric may limit excessive strain on the configured FEC during movements of the configured FEC that require stretching, and may provide static charge distribution and dissipation of charge accumulated through friction and environmental factors during use of the device. The mesh fabric may be electrically connected to a fixed potential, for example, a fixed potential of one or more electrical circuits of a device according to an embodiment of the system described herein, and may provide charge shedding for the one or more electrical circuits. The mesh fabric may be secured in place by flexible silicone (or similar material) encapsulation. In some embodiments, the mesh fabric may be configured to promote entanglement with the encapsulant. For example, the mesh fabric may have a coarse weave forming a lattice with relatively large openings. Such a coarse weave may facilitate the entrapment of the mesh fabric by a flexible encapsulant by enabling the encapsulant to fully envelop the fabric through the lattice openings. Embodiments of mesh fabrics are described in more detail elsewhere herein.

In other embodiments, a rigid (or semirigid) electromechanical construct (REC) may be used in place of the combination of the FEC and the mesh fabric or used with the mesh fabric. The REC has relatively rigid arms provide attachment points for electrodes at ends of the arms and provide physical and electrical interconnections for the electrodes. The rigid arms inhibit significant deformation of the REC by resisting longitudinal deformation in response to tensile or compressive radial forces and by providing a relatively small amount of deformation in response to forces that are orthogonal to the longitudinal axes of the arms. Thus, the REC may, on the one hand, conform to dynamic movement of limb and tissue while, at the same time, avoid damage associated with significant deformation that may occur when the REC is removed from a patient.

In some embodiments of the system described herein, a device including the configured FEC coupled to the electrode structures and overlayed with a mesh fabric may be formed by encapsulating these components using one or more flexible encapsulants, where the one or more flexible encapsulates themselves are part of the device. The encapsulating process may include arranging electrode structures within a first mold, for example, in a two-dimensional array. A first encapsulation may be performed that encapsulates the electrode structures with a first flexible encapsulant using a first molding process to produce a bottom part of the device. A configured FEC that processes biopotential signals may be positioned above the bottom part, and the configured FEC may be electrically coupled to the electrode structures. The configured FEC may be positioned within a second mold while the configured FEC is electrically coupled to the electrode structures, and a second encapsulation may be performed. The second encapsulation may include encapsulating the configured FEC with a second flexible encapsulant (which may be the same as the first flexible component) using a second molding process to produce a top part of the device. The second molding process may include bonding (e.g., permanently) the top part to the bottom part to form the device. The first and second encapsulants may have an elasticity equal to or greater than the configured FEC so that the encapsulated device may conform to the skin of a subject.

The top ends of electrodes of the electrode structures may be left exposed by the first encapsulation and connected to electrical contacts of the configured FEC. The bottom ends of electrode structures may be left exposed by the first and second encapsulations and form a bottom surface of the device along with the second flexible encapsulant. Electrode protrusions of the electrode structures may form part of the bottom surface and protrude from a plane of the bottom surface formed by the bottom surface of the non-conductive carrier and the bottom surface of the first flexible encapsulant, where such protrusions ultimately may depress into the skin of a subject. Embodiments of forming a device that include encapsulating components of the device are described in more detail elsewhere herein. The encapsulated device may be part of the system described herein, for example, along with a skin interface as described in more detail elsewhere herein. However, it should be appreciated that embodiments of the system described herein may include the encapsulated device without the skin interface, and such a system may be used to detect and process biopotential signals from a subject.

In some embodiments, a skin interface is provided that temporarily attaches an encapsulated device as described herein to skin, and may be configured to be disposable. The skin interface may include a substrate (e.g., silicone), a skin adhesive configured to adhere (e.g., temporarily) to skin, and a device adhesive configured to adhere (e.g., temporarily) to the device, for example, to a flexible encapsulant of the bottom surface of the device. The skin interface also may include a carrier layer configured on a same side of the substrate as the device adhesive and configured to adhere to bottom surfaces of electrode carriers of the device. The substrate, skin adhesive, device adhesive and carrier layer each may have openings aligning to the electrodes of the device, so that electrode protrusions protruding from the bottom of the device may protrude from the skin interface, for example, may protrude from a surface of the skin adhesive contacting the skin of the subject.

The skin interface may include an aligning layer (e.g., made of foam) on the device side of the skin interface having interior sidewalls that conform to at least a portion of an exterior side perimeter of the encapsulated device and assist in aligning the plurality of openings with the plurality of electrodes. The skin interface also may have a pull tab configured to enable removing the skin interface from the skin and from the device to which the skin interface is adhered. The skin interface may be configured to be at least as flexible as the encapsulated device so that the system may conform to the skin of a subject along with the encapsulated device. Embodiments of skin interfaces are described in more detail elsewhere herein.

In some embodiments, the system described herein may be arranged on the skin of a subject, and the system may be used to detect biopotential signals from the subject and process the signals. For example, the system may include a skin interface as described herein adhered to an encapsulated device as described herein and adhered to the skin of a subject so that electrode protrusions depress into the skin of the subject. In some embodiments, the system may be arranged so that a pattern (e.g., a two-dimensional array) of the electrodes of the system aligns, at least generally, to the muscle fibers of one or more muscles (e.g., of a muscle group) of the subject, or to another area of interest of the body of the subject. The system may be configured to conform to the surface of the skin of the subject.

In some embodiments, after being arranged on the skin of a subject, the system may detect and process biopotential signals. It should be appreciated that the biopotential signals detected at each electrode may result from bipotential signals emanating from multiple sources within the body of a subject, for example, from muscle fibers of multiple different muscles. Some of these muscles may be shallower within the body in relation to the surface of the skin from which biopotential signals are detected than other muscles. For example, for a given group of muscles, one or more muscles may reside at a shallow layer and one or more muscles may reside at a deeper layer relative to the surface of the skin at which biopotentials are being detected. In embodiments of the system described herein, the processing of a biopotential signal detected from an electrode may include determining an extent of the biopotential attributable to muscles at a deep layer vs. muscles at a shallow layer, and vice versa.

Prior to detecting biopotentials using the system, two or more electrodes of the system may be electrically connected to form a common electrical node, for example, using hardwiring, electrical programming, physical switching and/or logical switching. Biopotentials then may be detected from the plurality of electrodes of the system. The biopotential detected from the common electrical node may be used as a reference potential. For each of the remaining (non-common) electrodes of the system, a biopotential difference may be determined between a biopotential detected at the electrode and the reference potential, this difference representing a magnitude of the biopotential detected at this node.

Determining the biopotential difference between an electrode and a reference potential may include: 1) sampling (e.g., using an ADC) biopotentials at a predetermined frequency (the "sampling rate"), for example, between 1 KHz and 20 KHz, where the interval of time corresponding to the sampling rate is referred to herein as the "sampling interval;" and 2) determining a bipotential value (e.g., a root mean square (RMS) value) for a time period ("measurement period") that includes a plurality of the sampling intervals. For example, for a 1 KHz or 20 KHz sampling rate, the sampling interval would be 1 millisecond (ms) or 50 microseconds (μs), respectively, and the measurement period may be 50 ms or 2.5 ms, respectively. The measurement periods may be considered a sliding window of time, where the RMS value for a measurement period is an RMS of the biopotential differences detected for each sampling internal within the window of time that is the measurement period.

Further, each measurement period may be correlated to a particular time, and the RMS value calculated for the measurement period may be considered the magnitude of the biopotential difference for the particular time. For example, a biopotential difference value may be calculated for every 5 millisecond unit of time by calculating the RMS for the biopotential differences sampled (e.g., every 50 μs) during a measurement period of time that is 2.5 milliseconds in length, spanning 1.25 milliseconds of time before and after the unit of time for which the value is being calculated.

In some embodiments of the system described herein, the extent of a biopotential difference determined for a given electrode of the system for a first measurement period that is attributable to a deep layer of muscles may be determined by calculating a difference between: the biopotential difference (e.g., RMS value) determined for the given electrode for the first measurement period (correlated to a particular time); and a biopotential difference (e.g., RMS value) determined for another electrode of the system for a second measurement period (correlated to a particular time) that is a predefined amount of time offset from the first measurement period. The other electrode may be an electrode that is adjacent to the given electrode relative to other electrodes—i.e., may be a nearest electrode to the given electrode. For example, the electrodes may be arranged in a two-dimensional array of rows and columns, and the other electrode may be a nearest electrode on either side of the given electrode in the column.

As is explained in more detail elsewhere herein, the amount of the offset that results in a most accurate determination of the extent of a biopotential difference attributable to a deep layer of muscles may be determined iteratively. That is, biopotential differences (e.g., RMS values) determined for the other electrode may be determined for several different second measurement periods (correlated to particular times) that are offset different amounts of time from the first measurement period; and, for each of these second measurement periods, a difference may be calculated between: the biopotential difference determined for the given electrode for the first measurement period and a biopotential difference determined for the other electrode for the second measurement period. These calculated differences may be analyzed (e.g., compared to each other and/or other data previously detected, measured and/or calculated), to determine which amount of offset results in a most accurate determination of the extent of a biopotential difference attributable to a deep layer of muscles In some embodiments of the system described herein, the extent of a biopotential difference determined for a given electrode of the system for a first measurement period that is attributable to a shallow layer of muscles may be determined by making three separate difference determinations (in addition to biopotentials determined between electrodes and the reference potential). A first determination may include determining a difference between: the biopotential difference determined for the given electrode for the first measurement period; and a biopotential difference determined from a first adjacent electrode (e.g., in a column of the given electrode) for the first measurement period, which may be referred to as a first adjacent difference. A second determination may include determining a difference between: the biopotential difference determined for the given electrode for the first measurement period; and a biopotential difference determined from a second adjacent electrode (e.g., in the column of the given electrode) for the first measurement period. The first and second adjacent electrodes may be on opposite sides of the given electrode from each other, for example, in a same column as the given electrode. A third determination may determine a difference between the first adjacent difference and the second adjacent difference.

Any biopotential information detected, determined or processed by an embodiment of the system described herein may be stored in memory (e.g., non-volatile memory) of the device (e.g., on a configured FEC thereof) on which the information is detected, determined or processed, and may be communicated to other devices, wirelessly or otherwise, using one or more communication interfaces, which may be provided on the device. For example, the determined biopotentials, and differences determined therefrom, as described above, may be stored in data structures, e.g., tables. For example, one or more tables may include a plurality of entries (e.g., rows), each entry representing an electrode of a system described herein, or an electrode and a sampling interval, or an electrode and a measurement period. Each entry may include various detected and determined biopotential information corresponding to the electrode, sampling interval and/or measurement period. It should be appreciated that any of a variety of indexes may be created from such data structures.

In some embodiments, the biopotential information described herein may be detected, determined and processed for multiple locations (e.g., different muscle groups) of a subject, and/or for the same location (e.g., same muscle group) across multiple subjects, and from the resulting information a normative database of muscle depth location and depth information may be created. Such a database may be used for a variety of purposes, including producing visualizations of muscles and their function and activities.

It should be appreciated that, by increasing the number of electrodes in the system and/or decreasing the spacing between them, increased surface area coverage, increased specificity (e.g., the ability to resolve overlapping muscle sources) and increased range in depth may be obtained. For example, in an embodiment in which the electrodes are arranged in a two-dimensional array, columns may be made longer to cover more muscle length and more columns may be added to cover more muscle width.

Illustrative embodiments of the system described herein will now be described in more detail in relation to the figures.

Figure 1:
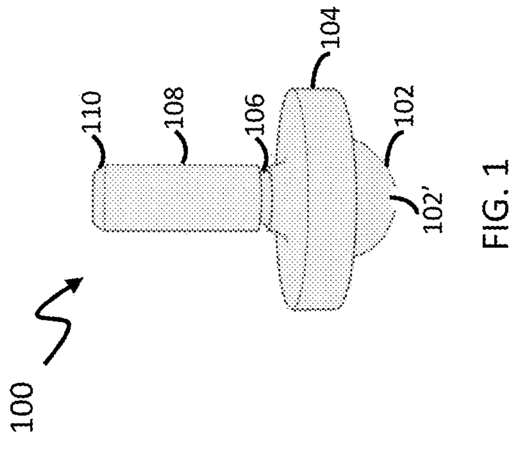
FIG. 1 is an electrode according to an embodiment of the system described herein.

FIG. 1 is an electrode 100 according to an embodiment of the system described herein. Other embodiments of an electrode, for example, variations of the electrode 100, are possible and are intended to fall within the scope of the invention. The electrode may be manufactured from essentially pure silver (e.g., 99.9% pure) in order to provide a stable skin-electrode interface, or from other metals, metal alloys or other conductive materials that have desirable qualities that minimize skin potential offset errors and minimize noise artifacts during movement. As illustrated in FIG. 1, the electrode may have a generally cylindrical shape.

The electrode 100 may include any of: a protruding portion (i.e., protrusion) 102; a flange portion (i.e., flange) 104; an inset ring 106; a cylindrical portion (i.e., post) 108; and a chamfered edge 110 of the post 108. The protrusion 102 may have a hemispherical shape like a dome or have other shapes. The protrusion 102 may have a smooth, bur-free surface that depresses into the skin of a subject when a system as described herein is in operation. In some embodiments, the protrusion 102 may include a cavity 102' (e.g., a dimple) that holds a droplet of moisture of ionic gel to minimize skin noise and maximize biopotential detection to the extent possible.

The flange 104 may serve as a mechanism by which an electrode carrier (e.g., the electrode carrier 200) can provide a tight seal around the electrode to prevent ingress of moisture (e.g., from the skin of subject in contract with the protrusion 102) to the remainder of the electrode 100 and the remainder of the system, in particular the FEC (e.g., the FEC 300). The flange 104 may have a diameter greater than the protrusion 102, the inset ring 106 and the post 108. A bottom surface of the flange 104 may serve as an annular section of the bottom surface of the electrode 100, where a remaining portion of the bottom surface of the electrode may be formed from a surface of the protrusion 102 protruding out of the bottom of the electrode 100.

The inset ring 106 (e.g., a swage ring) may assist in encasing the electrode 100 in an electrode carrier, and may have a diameter less than the diameter of the flange 104 and the post 108. For example, encasing the electrode 100 may include soldering the material (e.g., printed circuit board) of an electrode carrier around the electrode 100, and the inset ring 106 may assist in retaining the carrier material against the electrode 100. The insert ring 106 may further serve to provide an interface joint with the carrier material to prevent capillary wicking of moisture from the exterior of the electrode 100, e.g., from where the protrusion 102 contacts skin, to the remainder of the electrode 100 and the remainder of the system in which the electrode 100 is connected.

The post 108 may be the part of the electrode that is (or is expected to be) electrically coupled to a configured FEC of a system as described herein. For example, the post 108 may be received by, and mechanically and electrically coupled (e.g., soldered) to, a contact of a configured FEC; e.g., to an eyelet of the contact. A top end of the post 108 may include the chamfered edge 110, which may remove burs from the top edge of the post 108 during formation and may ensure self-alignment when coupled (e.g., soldered) to a contact (e.g., eyelet) of a configured FEC.

FIG. 2A is an exploded view of an electrode structure 200 according to an embodiment of the system described herein. Other embodiments of an electrode structure 200, for example, variations of the electrode structure 200, are possible and are intended to fall within the scope of the invention. The electrode structure 200 may include electrode 100 encased in an electrode carrier 202 so that a portion of the electrode fits in the electrode carrier 202. That is, a portion of the electrode 100 that is encased in the electrode structure fits around and has a same shape as a portion of the electrode carrier 202 that accepts the portion of the electrode 100.

The carrier 202 may have a cylindrical shape and may be configured to create a hermetic and waterproof seal around the post 108 of the electrode 100 to prevent an influx of moisture. The carrier 202 also may serve as an interface between the electrode 100 and an encapsulant of an encapsulated device including the electrode structure 200, as described in more detail elsewhere herein. A bottom surface 206 of the carrier 202 may be a smooth, rigid, cleanable surface, for example, to which a medical grade adhesive tape may adhere for holding the electrode 100 against the skin of a subject, as described in more detail elsewhere herein. For example, the bottom surface 206 may serve as a bottom surface of an encapsulated device as described herein, for example, in place of a flexible encapsulant, which be made of a material (e.g., silicone) that presents adhesion challenges.

The carrier 202 may have a center opening 208 that accommodates the post 108 of the electrode 100. The carrier 202 may include an inset portion 204 that has a diameter less than the diameter of the remainder of the carrier 202. The inset portion may provide an interference profile to seal against an encapsulant of an encapsulated device as described herein that includes the electrode structure 200, and may serve to assist in preventing the transfer of moisture from the exterior of such an encapsulated device into the device via the electrode 100. The cylindrical side wall 203 of the carrier 202, including the sidewalls of the inset portion 204, may provide a contact surface for an encapsulant, as described in more detail elsewhere herein.

Figure 2B:
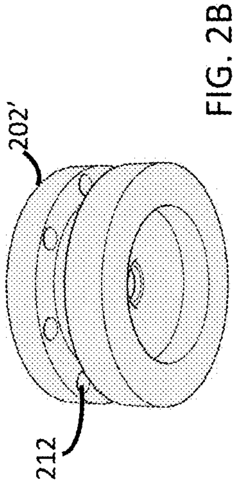
FIG. 2B illustrates a carrier of an electrode structure according to an embodiment of the system described herein.

FIG. 2B illustrates an alternative carrier 202' that is similar to the carrier 202 discussed in connection with FIG. 2A. The alternative carrier 202' includes one or more perforations 212 provided on a surface thereof to augment encapsulant bonding. The perforations may create a mechanical interference which helps counter a tendency for silicone to separate from the carrier 202' during excessive substrate stretch.

Figure 3A:
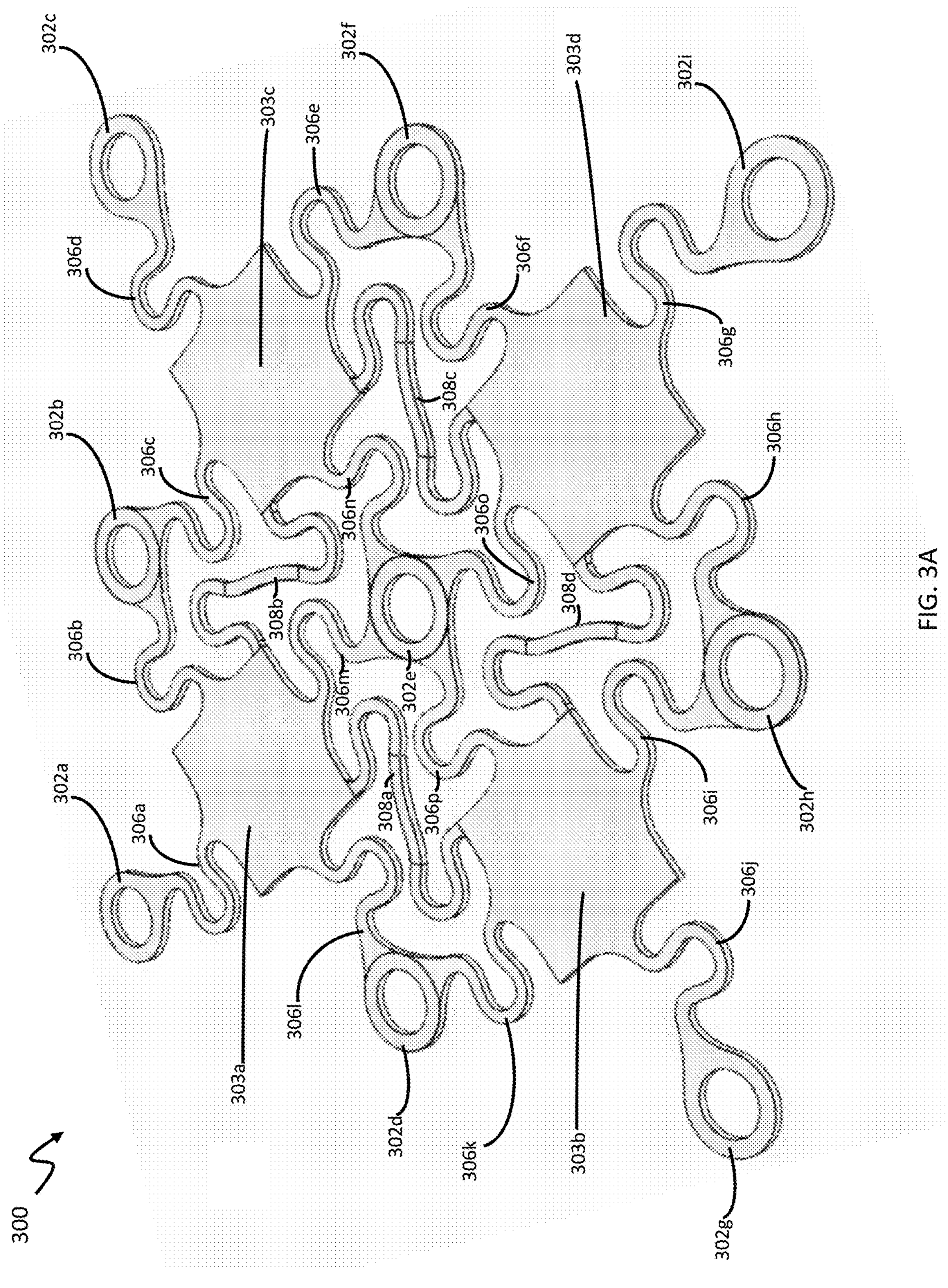
FIG. 3A illustrates a flexible electromechanical construct according to an embodiment of the system described herein.

FIG. 3A illustrates a flexible electromechanical construct (FEC) 300, according to an embodiment of the system described herein. Other embodiments of an FEC, for example, variations of the FEC 300, are possible and are intended to fall within the scope of the invention.

The FEC 300 may include a plurality of conductive contacts 302*a-l*, e.g., in the form of eyelets. The FEC 300 may include less or more than the nine contacts shown, and may include a same number of contacts as there are electrodes in embodiments of the system described herein. Each contact 302*a-i* may be configured to be mechanically and electrically coupled (e.g., soldered) to an electrode (e.g., the electrode 100) of an electrode structure (e.g., the electrode structure 200), for example, to the post 108 of the electrode 100.

The FEC 300 may include a plurality of islands 303*a-d*, where each island may serve as a platform for any of a variety of components, for example, at least a portion of the electrical circuitry and other electronic components described herein. There may be more or less than the four islands 303*a-d* illustrated. Each island 303*a-d* may be manufactured as a multi-layer construct, for example, using known fabrication techniques, and may include a plurality of materials, including conductive materials and semi-conductive materials. For example, each island 303*a-d* may include multiple layers and channels to enable electrical connection (e.g., through conductive and semi-conductive material) between electrical components (e.g., PCBs) on the islands and connectors described in more detail elsewhere herein. For example, each island 303*a-d* may be configured to receive pins of a PCB.

Each of the islands 303*a-d* may be connected to one or more contacts 302*a-i* by one or more connectors 306*a-l*, which may be referred to herein as "contact connectors," and may be connected to one or more other islands 303*a-d* by one or more other connectors 308*a-d*, which may be referred to herein as "inter-island connectors" ("IICs"). The contact connectors 306*a-l* and IICs 308*a-d* collectively may be referred to herein as "connectors," and the singular term "connector" may be used herein to generically refer to a contact connector or IIC. Each of the contact connector 306*a-l* may include conductive material and, as described in more detail elsewhere herein, may include one or more electrical communication paths to conduct a biopotential signal detected at an electrode from a contact coupled to the electrode to one or more of the islands 303*a-d*, for example, to a pin of a PCB on one of the islands 303*a-d*, as described in more detail elsewhere herein. The IICs 308*a-d* may allow PCBs on the islands 303*a-d* to exchange information and instructions with each other as part of processing detected biopotentials, for example, as part of a distributed computational system as described herein.

Each connector may be manufactured as a multi-layer construct, for example, using known fabrication techniques. For example, the connectors may include multiple layers and channels to implement a plurality of electrical communication channels between islands and/or contacts, the details of which are not illustrated in FIG. 3A. Each connector may include a plurality of materials, including conductive materials, semi-conductive materials and/or reinforced fiber glass. Each of the connectors may be elastically deformable to enable electrodes to which the contacts may be coupled to be moved in three dimensions and to enable the FEC 300 to conform to the contours of a non-uniform surface, for example, the skin of a subject as part of a system as described herein. For example, each connection may have a serpentine shape and be bendable relative to both dimensions of a lateral plane formed between islands and/or contacts, and may be stretchable and compressible along such a plane. Thus, the FEC 300 may involve movement of limb and tissue when part of a system described herein may be able to dynamically conform to the contours of the skin of a subject during muscle activity.

Figure 3B:
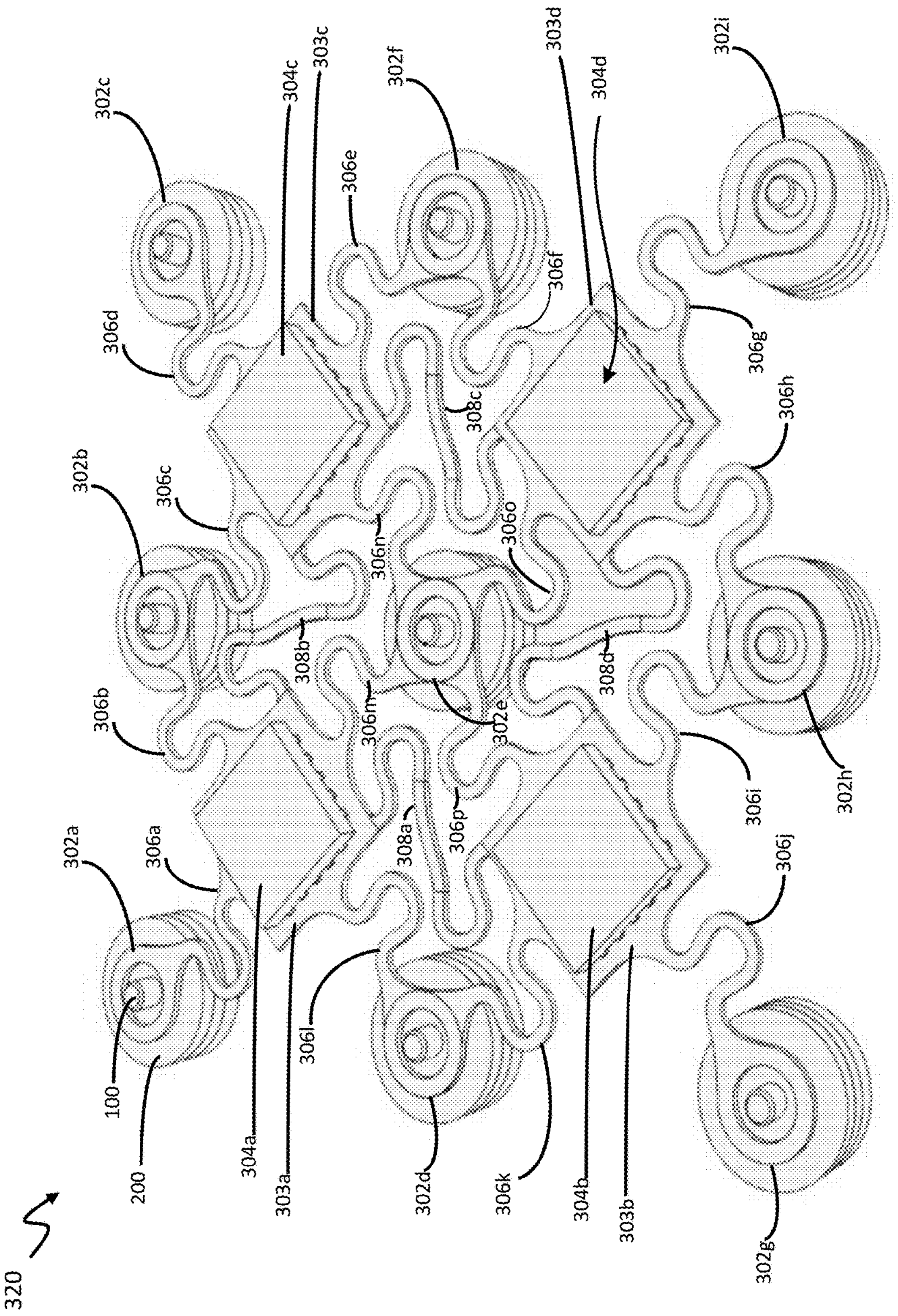
FIG. 3B illustrates a flexible electromechanical construct connected to electrode structures and printed circuit boards according to an embodiment of the system described herein.

FIG. 3B illustrates a configured FEC 320 connected to electrode structures (e.g., the electrode structure 200) according to an embodiment of the system described herein. Each contact 302*a-i* of the configured FEC 320 may be mechanically and electrically coupled (e.g., soldered) to an electrode (e.g., the electrode 100) of an electrode structure (e.g., the electrode structure 200), for example, to the post 108 of the electrode 100. The configured FEC 320 may be the FEC 300 with one or more of the PCBs 304*a-d* residing on each of the islands 303*a-d*, where each PCB may include at least a portion of the electrical circuitry and other electronic components described herein. Each of the PCBs 304*a-d* may have one or more pins to connect to electrical conductors within the islands 303*a-d*. There may be more or less than the four PCBs 304*a-d* illustrated. Each of the PCBs 304*a-d* may be electrically coupled to one or more electrodes (e.g., an electrode 100) via one or more electrical communication paths, each such path including one or more paths within the islands 303*a-d*, one or more paths within contact connectors 306*a-l* and one of the contacts 302*a-i*. Each of the PCBs 304*a-d* may be electrically coupled to other ones of the PCBs 304*a-d* by electrical communication paths configured within the islands 303*a-d* themselves and within the IICs 308*a-d*.

Each of the contact connectors 306*a-l* may include one or more electrical coupling paths that electrically couple a biopotential signal detected at an electrode from the contact coupled to the electrode to one or more of the PCBs 304*a-d*, for example, to a pin of each of the one or more PCBs 304*a-d*. The IICs 308*a-d* may allow the PCBs 304*a-d* to exchange information and instructions as part of processing detected biopotentials, for example, as part of a distributed computational system as described herein.

Each of the PCBs 304*a-d* may be located on an island at any location of the configured FEC 320, e.g., along the periphery, near the center or somewhere in between. In some embodiments, more centrally located PCBs may be used to distribute the biopotential processing logic, and more peripherally located PCBs may be used to aggregate other components of the configured FEC 320 and/or to allocate contact points for cable assemblies to service the biopotential processing logic.

The resulting combination of the configured FEC 320 (including the PCBs 304*a-d*) and the coupled electrodes within electrode carriers thereof may be considered a distributed, flexible mesh network that couples electrodes to biopotential processing logic.

Figure 3C:
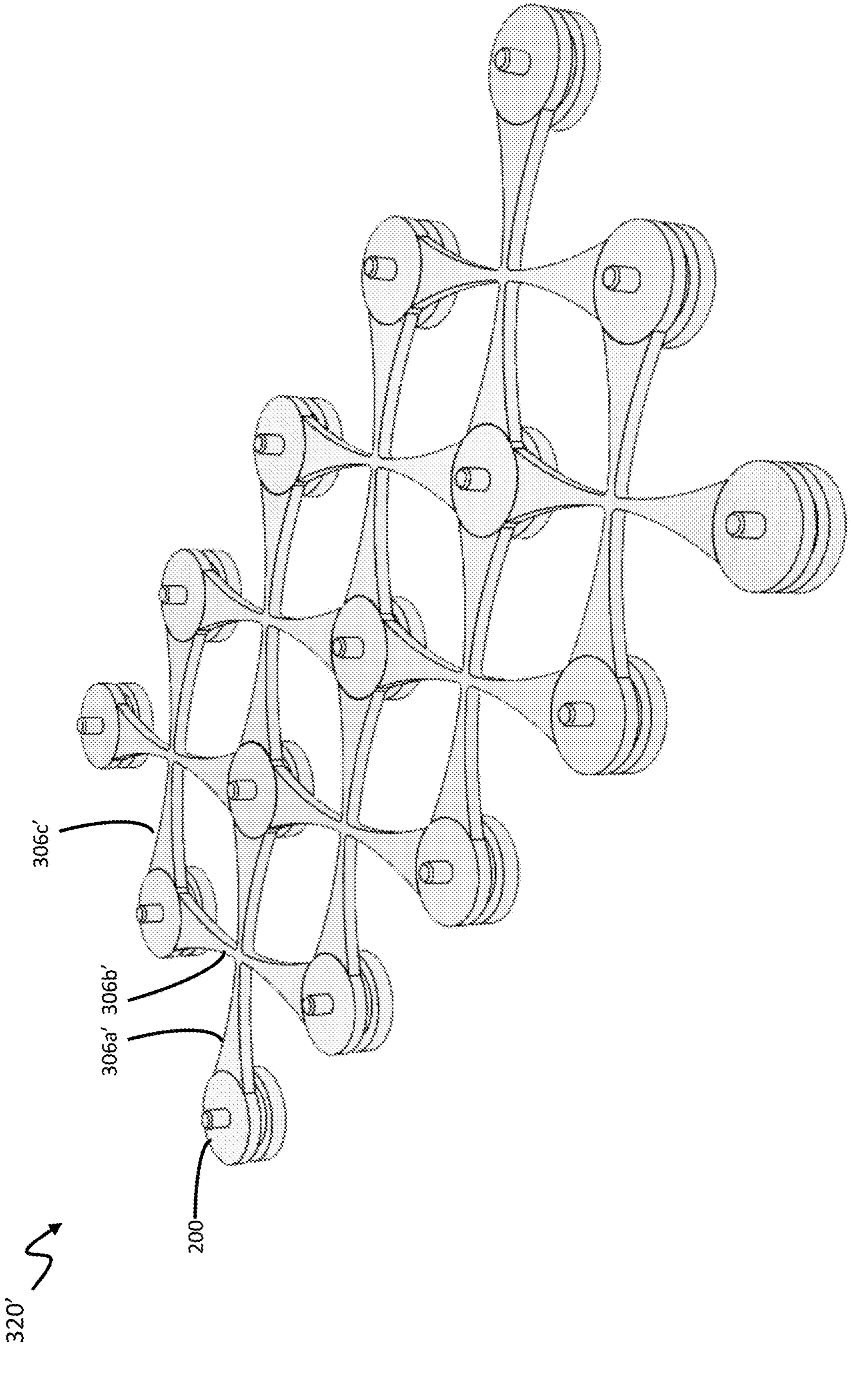
FIG. 3C illustrates a rigid or semirigid electromechanical construct connected to electrode structures according to an embodiment of the system described herein.

FIG. 3C illustrates a rigid (plastic) or semirigid (e.g., stiff silicone) electromechanical construct (REC) 320' connected to electrode structures (e.g., the electrode structure 200) according to an embodiment of the system described herein. The REC 320' may be used as an alternative to or together with the FEC 320 of FIG. 3B. A plurality of relatively rigid (plastic) or semirigid (stiff silicone) arms 306*a*', 306*b*', 306*c*' provide attachment points for electrode structures at ends of the arms 306*a*', 306*b*', 306*c*' and provide interconnections for the electrode structures. The arms 306*a*', 306*b*' are fixedly interconnected at midsections thereof (i.e., not at the ends) to provide stiffness to the REC 320'.

The attachment points may act like bearings so that the arms 306*a*', 306*b*', 306*c*' may deform (e.g., freely rotate). For example, an angle formed by the arms 306*b*', 306*c*' may change as one or both of the arms 306*b*', 306*c*' deforms/rotates about the attachment point of the arms 306*b*', 306*c*'. One or more PCBs (not shown in FIG. 3C), like the PCBs 304*a*-304*d* of FIG. 3B, may be provided at intersections of the arms 306*a*', 306*b*' and/or at any other appropriate location. Each of the PCBs may include at least a portion of the electrical circuitry and other electronic components described herein and may be electrically coupled to one or more electrode structures via one or more electrical communication paths.

Functionally, the REC 320' is similar to the FEC 320 that is described in FIG. 3B. However, the rigid or semirigid arms 306*a*', 306*b*', which are attached at midsections thereof, inhibit significant deformation of the REC 320' by resisting longitudinal deformation in response to tensile or compressive radial forces and by providing a relatively small amount of deformation in response to forces that are orthogonal to the longitudinal axis of the arms 306*a*', 306*b*', 306*c*'. Thus, the REC 320' may, on the one hand, conform to dynamic movement of limb and tissue like the FEC 300, 320 while, at the same time, avoid damage associated with significant deformation that may occur when the REC 320' is removed from a patient.

Figure 4:
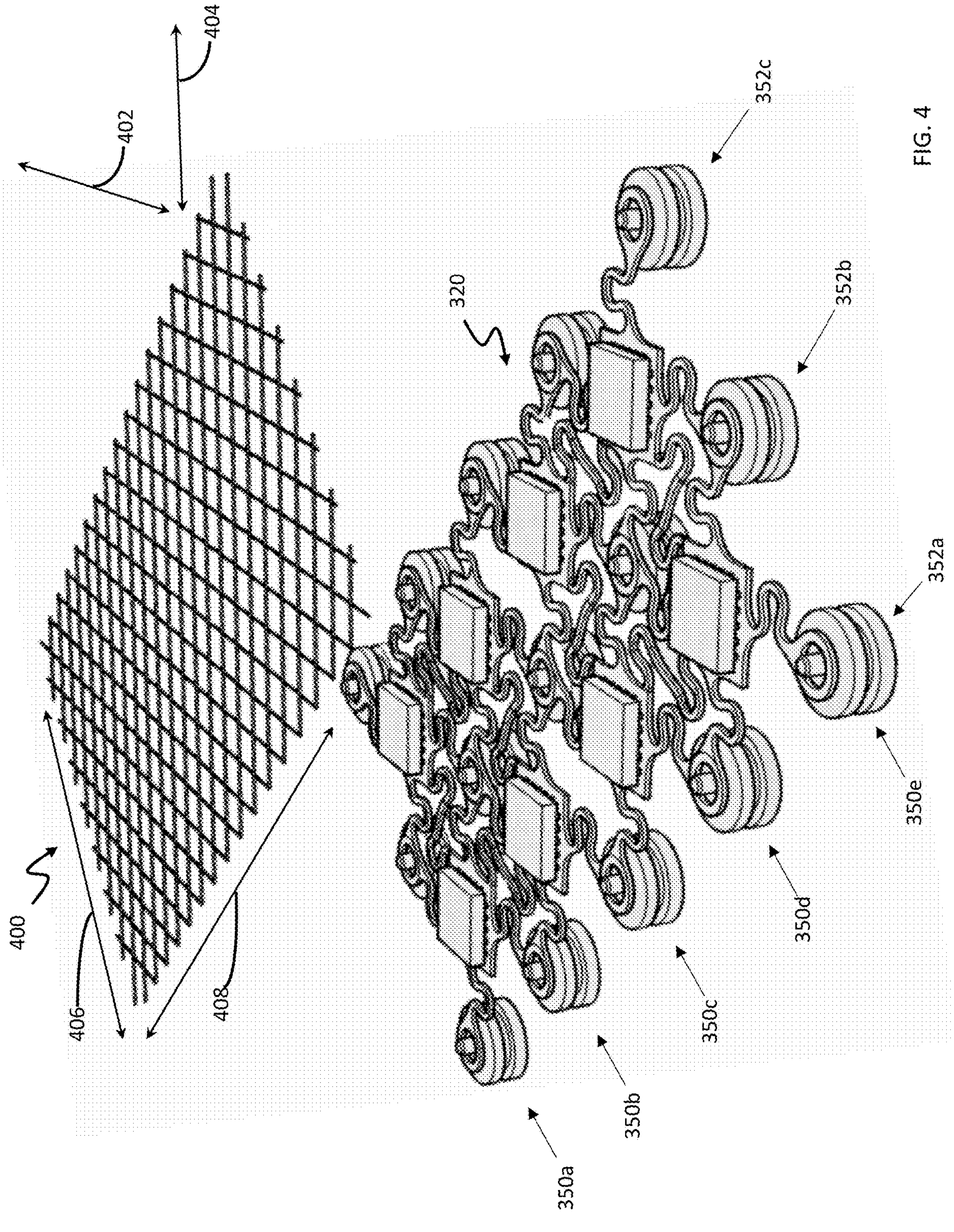
FIG. 4 is a perspective view of a mesh fabric and an electromechanical device connected to electrode structures according to an embodiment of the system described herein.

FIG. 4 is a perspective view of a mesh fabric 400 and the configured FEC 320 connected to electrode structures according to an embodiment of the system described herein. Other embodiments of a mesh fabric, for example, variations of the mesh fabric 400, are possible and are intended to fall within the scope of the invention. For example, the mesh fabric 400 may be configured to work with the REC 320' instead of or in addition to the FEC 320. The mesh fabric 400 may overlay the configured FEC 320 as part of a system as described herein, for example, as part of an encapsulated device. The mesh fabric 400 may include a plurality of fibrous threads arranged as a grid in which a first subset of the threads align in a first direction 402 and a second subset of the threads align in a second direction 404 orthogonal to the first direction 402. In some embodiments, the electrical contacts (e.g., eyelets) of the configured FEC 320 and the electrode structures to which they are coupled are arranged in a two-dimensional array including rows 350*a-e* along a third direction 408 and columns 352*a-c* along a fourth direction, each of the third and fourth directions being oblique to both the first direction 402 and the second direction 404 in which the grid threads are aligned.

The mesh fabric 400 may be elastically deformable. When a system as described herein for detecting and processing biopotential signals including the configured FEC 320 and the mesh fabric 400 is adhered to the skin of a subject, the mesh fabric 400 may bear the mechanical strain of the configured FEC 320 when the mesh fabric 400 is stretched to conform to the skin of a subject, for example, during dynamic movement of tissue (e.g., muscles) beneath the skin. For example, the mesh fabric may be configured to bear up to a certain amount of strain (e.g., 120%) in the first direction 402 and up to a certain amount of strain (e.g., 120%) in the second direction 404.

The fibrous threads of the mesh fabric 400 may be made of natively conducting material (e.g., metal wire) or of non-conductive material coated with a conductive finish, such that the mesh fabric 400 may provide static charge distribution and dissipation of charge accumulated through friction and environmental factors during use of the system. The mesh fabric 400 may be electrically connected to a fixed potential, for example, a fixed potential of the configured FEC 320, and may provide charge shedding for one or more electrical components of the configured FEC 320. The mesh fabric 400 may be secured in place proximate to a top surface of the configured FEC 320 by flexible silicone (or similar material) encapsulation. In some embodiments, the mesh fabric 400 may be configured to promote entanglement with the encapsulant. For example, the mesh fabric 400 may have a course weave forming a lattice with relatively large openings. Such a course weave may facilitate the entrapment of the mesh fabric 400 by a flexible encapsulant by enabling the encapsulant to fully envelop the fibrous threads of the mesh fabric 400 through the lattice openings.

Note that, in some embodiments, the REC 320' may replace the combination of the mesh fabric 400 and the FEC 320 or simply replace just the mesh fabric 400. In such a case, the REC 320' may bear the mechanical strain in both directions 402, 404 that would otherwise be imposed on the mesh fabric 400 when the mesh fabric 400 is used with the FEC 320.

Figure 5:
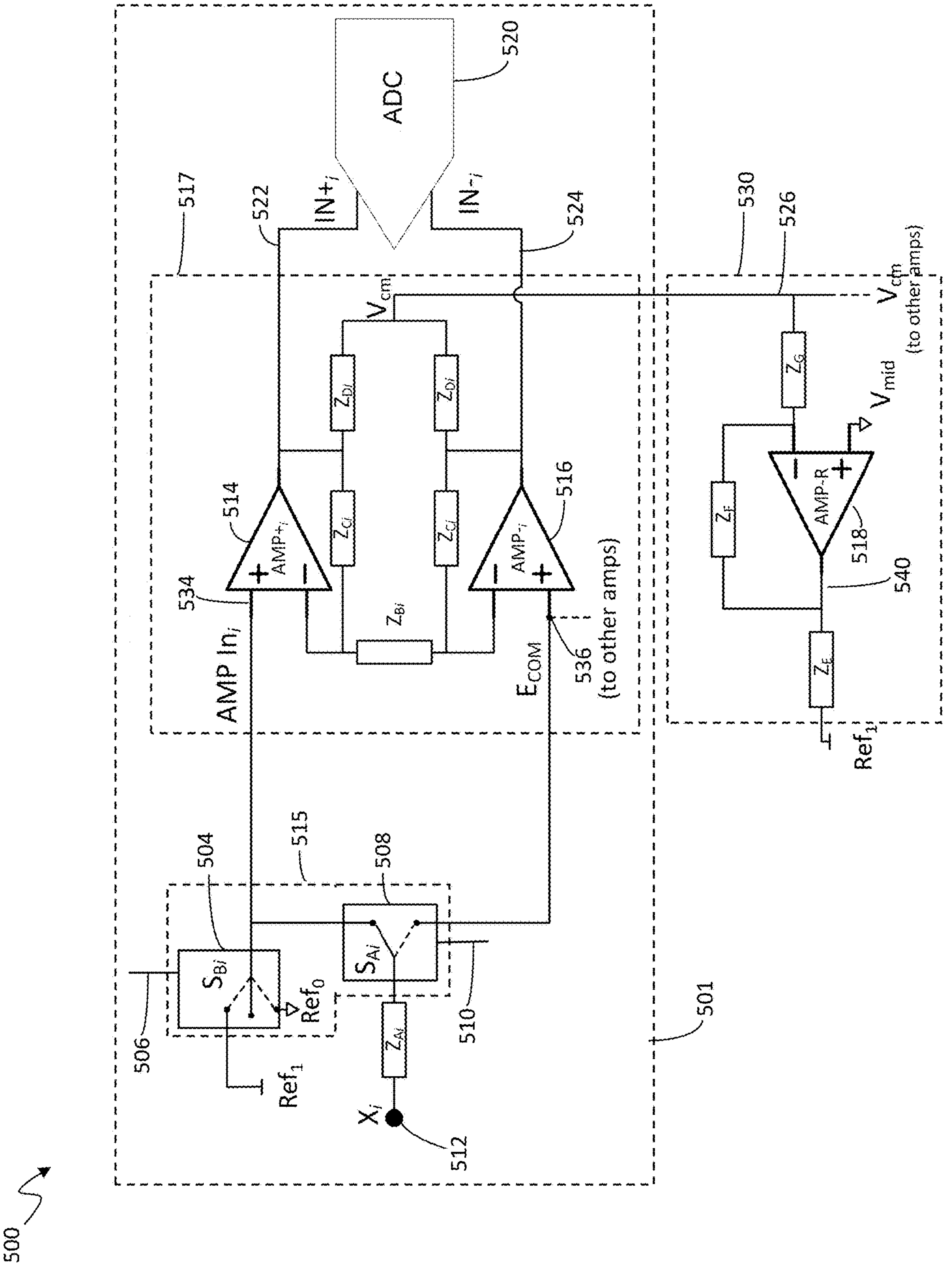
FIG. 5 is a circuit block for determining a biopotential detected by an electrode, according to an embodiment of the system described herein.

FIG. 5 illustrates an electrical circuit 500 for determining a biopotential detected by an electrode, according to an embodiment of the system described herein, where each section may be referred to herein as a circuit block. Other embodiments of the circuit 500, for example, variations of the circuit 500, are possible and are intended to fall within the scope of the invention. The circuit 500 may include: a plurality of circuit blocks 501; noise cancellation circuitry 530; other components; or any suitable combination of the foregoing. The circuit 500 may include one circuit block 501 for each electrode of a system for detecting and processing biopotentials in which the circuit is included. For example, for the configured FEC 320, which has fifteen electrodes, the circuit 500 may have fifteen circuit blocks 501. The electrical circuit 500 may be implemented on one or more of the PCBs 304*a-d* of the configured FEC 320, for example, by soldering the electrical circuit 500 onto one or more of the PCBs 304*a-d* in a die form and/or in a ceramic IC package form.

Each of the circuit blocks 501 may include any of: switching circuitry 515; differential amplifier circuitry 517; ADC circuitry 520; other components; or any suitable combination of the foregoing. The differential amplifier circuitry 517 may be a symmetrical non-inverting differential amplifier arrangement including differential operational amplifiers (op amps) 514, 516. The output of the differential amplifier circuitry 527 may be defined by a difference between output voltages 522, 524 of the op amps 514, 516, which serve as inputs $IN+_i$ and $IN-_i$ of the ADC circuitry 520, which may be differential ADC circuitry. A gain of the differential amplifier circuitry 517 may be controlled by relatively low impedance elements $Z_{Bi}$ and $Z_{Ci}$, which may contain resistive, capacitive and inductive components. The components of the impedance elements $Z_{Bi}$ and $Z_{Ci}$ may be selected to amplify the biopotential signals received at amplifier inputs 534, 536 that are within a certain frequency range, while not amplifying out-of-band signals and within-band noise signals including direct current (DC) offset potentials. For example, the impedance elements $Z_{Bi}$ and $Z_{Ci}$ may be configured to amplify biopotential signals corresponding to the biological phenomena being analyzed, such as, for example, biopotentials radiating from muscle cells triggered by motor neuron excitement, e.g., biopotential signals within a bandwidth of 10-500 Hz.

The $Z_{Di}$ elements of the differential amplifier circuitry 517 may be resistive with optional capacitive and inductive elements, and may be used to generate a global common mode potential 526, $V_{cm}$, which sums the voltages of all the $V_{cm}$ points of the circuit blocks 501, and is indicative of a noise level detected by the amplifier circuitry 517. The global common mode potential 526, $V_{cm}$, may be input to noise cancellation circuitry 530. The noise cancellation circuitry 530 may include an operation amplifier 518 that inverts a difference between the global common mode potential 526 and a mid-supply reference $Ref_0$, with a gain factor determined by impedance elements $Z_{Di}$, $Z_F$ and $Z_G$, to produce an amplifier output 540 that then passes through an impedance element $Z_E$ to produce a noise cancellation signal, i.e., reference signal, $Ref_1$. The impedance element $Z_E$ may include resistive and capacitive elements to limit injection current to a certain amount, e.g., 100 uA or less, and remove out-of-band noise signals. The reference signal $Ref_1$ also may be imposed on the skin of a subject by direct electrical connection with one or more electrodes, as described in more detail elsewhere herein.

The switching circuitry 515 may include a first switch 508 ($S_{Ai}$) and a second switch 504 ($S_{Bi}$). The first switch 508 and the second switch 504 may be controlled, for example, by control inputs 510, 506, respectively, to select from multiple inputs. The first switch 508 may receive a biopotential signal 512, Xi, after the biopotential signal 512 passes through a resistive element $Z_1$, which may serve as a safety block to limit leakage current to a relatively low amount (e.g., 10 uA or less) in the case of a device fault. The control signal 510 may control whether the biopotential signal 512 is provided as the amplifier input 534 or as the amplifier input 536, which may serve as a common reference node of equipotential, and which may be referred to herein as a reference node or equipotential node, $E_{COM}$ or $E_c$. As illustrated in FIG. 5, the amplifier inputs 536 of all of the circuit blocks 501 may be directly electrically coupled together to form a single common node, Ec, among all of the circuit blocks 501, with at least one of the first switches 508 of the plurality of circuit blocks directly electrically coupling the common node Ec to an electrode contacting skin, as described in more detail herein.

The second switch 504 may receive reference potential $Ref_1$, determined based on current circuit noise, and a mid-supply (e.g., static) reference potential, $Ref_0$. The control signal 506 may control whether reference potential, $Ref_0$ or reference potential $Ref_1$, is provided as the amplifier input 534.

As is described in more detail elsewhere herein, one electrode of a system for detecting and processing biopotentials, or multiple electrodes of such a system directly coupled together (e.g., “tied” together), may serve as an equipotential node, $E_c$, from which biopotential differences with other electrodes of the system may be determined. For the circuit block 501 for each such electrode: 1) the control signal 510 may control the connection of the biopotential signal 512 detected from the electrode to the amplifier input 536 to serve as the equipotential node, $E_c$; and 2) the control signal 506 may control the selection of the static reference signal, $Ref_0$, or the noise cancellation reference signal, $Ref_1$, whichever is being used as the preferred reference signal of the circuit 500 (which may depend on the level of noise present). For each such electrode that serves as the equipotential node, the difference between the output voltages 522, 524 of the op amps 514, 516 for the circuit block corresponding to the electrode may not be sampled by the ADC 520.

The noise cancellation reference signal $Ref_1$ or the mid-supply reference signal $Ref_0$ may be imposed on the skin of a subject by direct electrical connection with one of the electrodes. This equates the skin potential to the circuit operating potential. In conditions where a common mode noise current is coupled to skin (such as when the device is being used near mains-powered electrical equipment), using the REF1 noise cancelling reference may mitigate the impact of the common mode noise by subtracting the noise from the system. For the circuit block 501 for each such electrode: 1) the control signal 510 may control the connection of the biopotential signal 512 detected from the electrode to the amplifier input 534; and 2) the control signal 506 may control the selection of the static reference signal, $Ref_0$, or the noise cancellation reference signal, $Ref_1$, whichever is being used as the preferred reference signal of the circuit 500. As a result, the electrode (and thus the skin of the subject) are electrically coupled to the selected reference potential. As the noise cancellation reference signal Ref1 is an inverse of the common mode potential 526, which is indicative of the noise level detected by the amplifier circuitry 517, coupling $Ref_1$ to the skin of the subject in effect cancels the noise. For each such electrode electrically coupled to a reference potential, the difference between the output voltages 522, 524 of the op amps 514, 516 for the circuit block corresponding to the electrode may not be sampled by the ADC 520.

For the circuit block 501 for any electrode (of a system for detecting and processing biopotentials as described herein) for which a biopotential difference between the biopotential detected by the electrode and the common node, Ec, is being detected: 1) the control signal 510 may control the connection of the biopotential signal 512 detected from the electrode to the amplifier input 534; and 2) the control signal 506 may control no selection of either the static reference signal, $Ref_0$, or the noise cancellation reference signal, $Ref_1$. For the circuit block 501 for each such electrode for which a bipotential difference is being determined, the difference between the output voltages 522, 524 of the op amps 514, 516 is the difference between the biopotential detected by the electrode and the biopotential of the common node, Ec; and, accordingly, the difference between the output voltages 522, 524 of the op amps 514, 516 is sampled by the ADC 520.

The circuit 500 may be part of an electronic system for detecting and processing biopotentials, for example, an electronic system, which will now be described.

Figure 6:
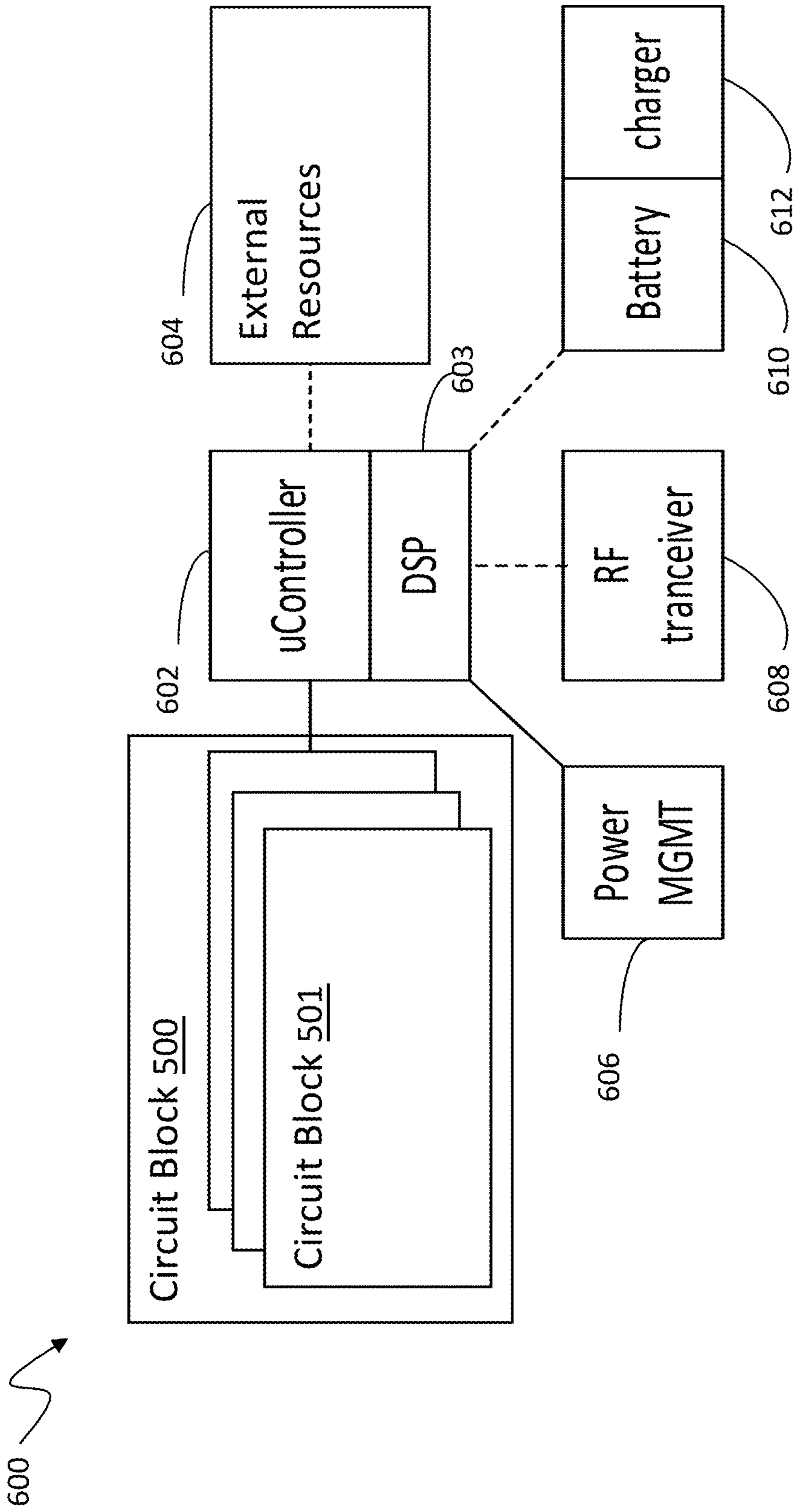
FIG. 6 is a block diagram of an electronic system for detecting and processing biopotentials according to an embodiment of the system described herein.

FIG. 6 is a block diagram illustrating an electronic system 600 for detecting and processing biopotentials, according to an embodiment of the system described herein. Other embodiments of an electronic system for detecting and processing biopotentials, for example, variations of the electronic system 600, are possible and are intended to fall within the scope of the invention. The electronic system 600 may include any of: the circuit 500 including a plurality of the circuit blocks 501; a microcontroller 602, a digital signal processor (DSP) 603; external resources 604; power management logic 606; a radio frequency (RF) transceiver 608; a battery 610; a battery charger 612; other components; or any suitable combination of the foregoing.

In some embodiments, the circuit blocks 500, the microcontroller 602, the DSP 603, the power management logic 606, the radio frequency (RF) transceiver 608 and/or the battery 610 are implemented on one or more PCBs of the configured FEC 320 and/or the REC 320'. In some embodiments, one or more of such components may be part of an encapsulated device as described herein, but not be implemented on the configured FEC 320 and/or the REC 320'. The external resources 604 may include computer, network and memory resources that are located external to the system described herein, for example, public or private networks, storage systems, servers, end-user devices, etc.

The microcontroller 602 and/or the DSP 603 may be configured to control the sampling rate (e.g., 1000-20,000 times per second) and to process the sampled biopotential differences. Processing the biopotential differences may include determining, for each predefined measurement period, an RMS value of the values sampled during the measurement period, where the RMS value serves as the determined biopotential difference for an electrode for a given measurement period. The DSP 603 may employ signal conditioning that results in a target bandpass of 20 Hz-450 Hz, may apply a digital filter that targets a maximally flat pass band area (e.g., <0.5 dB variation) to preserve biopotential amplitude information, and may use linear phase response to preserve biopotential temporal information. In some embodiments, the ADC circuitry 520 may produce a highly granular digital value (e.g., 24 bits), which may reduce processing resources required (e.g., by the DSP 603) to condition the sampled biopotentials.

The RF transceiver 608 may communicate information between components that are part of the configured FEC 320 and/or the REC 320', an encapsulated device as described herein and/or a system as described herein to components that are not part of the configured FEC 320 or the REC 320', encapsulated device and/or system, respectively. The power management logic 606 may manage power on the electronic system, or only certain components thereof, e.g., the encapsulated device or the configured FEC 320 and/or the REC 320'.

In some embodiments of the system described herein, at least a portion of the system is encapsulated, for example, with a flexible, hermetic and waterproof encapsulant. For example, a device including the configured FEC 320 coupled to the electrode structures 200 and overlayed with a mesh fabric 400 may be formed by encapsulating these components using one or more flexible encapsulants, where the one or more flexible encapsulants themselves form part of the device.

Figure 7:
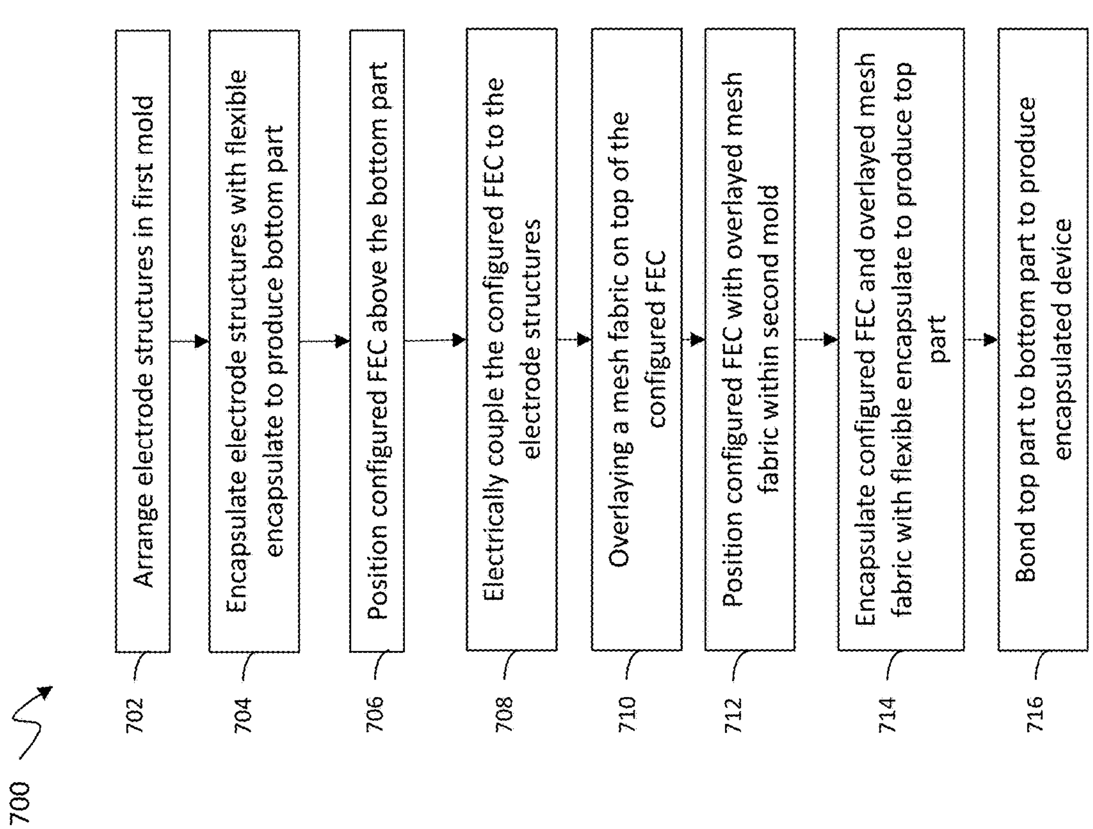
FIG. 7 is a flowchart of a method of encapsulating at least a portion of a system for detecting and processing biopotentials, according to an embodiment of the system described herein.

FIG. 7 is a flowchart 700 illustrating encapsulating at least a portion of a system for detecting and processing biopotentials, according to an embodiment of the system described herein. Other embodiments of encapsulating at least a portion of a system for detecting and processing biopotentials, for example, variations of the steps illustrated in the flowchart 700, are possible and are intended to fall within the scope of the invention.

FIGS. 8A-H illustrate a device for detecting and processing biopotentials, and portions thereof, at various stages of encapsulation, according to an embodiment of the system described herein, and will be referred to herein throughout the description of the flowchart 700.

In a step 702, electrode structures (e.g., the electrode structures 200) may be arranged in a first mold (e.g., a compression mold), for example, in a two-dimensional array. Prior to the step 702, the electrode structures may have been formed by encapsulating each of a plurality of electrodes (e.g., the electrode 100) in a plastic carrier 202 using any of a variety of known techniques, for example, soldering.

In a step 704, the electrode structures may be encapsulated with a first flexible encapsulant within the mold to form a bottom part of a device. The first flexible encapsulant may be a form of silicone or materials with similar suitable properties. The step 704 may include the flexible encapsulant surrounding and sealing (e.g., hermetically sealing) the sides of each electrode structure. However, a bottom surface of each electrode structure, including a bottom surface of the carrier and a protrusion (e.g., the protrusion 102) of the electrode may remain exposed at completion of the encapsulation process that forms the bottom part. The exposed bottom surfaces of the electrode structures combined with a bottom surface of the encapsulant may form a continuous bottom surface of the bottom part of the device, with the electrode protrusions protruding from the bottom part.

Figure 8B:
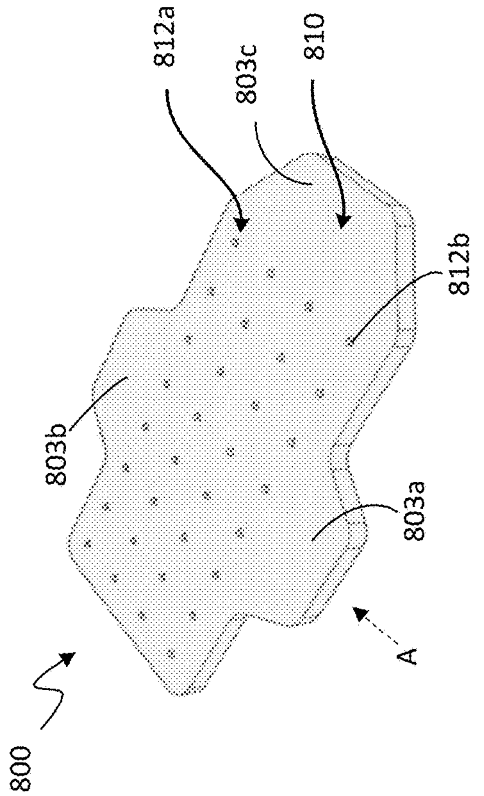
FIGS. 8A-H illustrate a device for detecting and processing biopotentials, and portions thereof, at various stages of encapsulation, according to an embodiment of the system described herein.
Figure 8A:
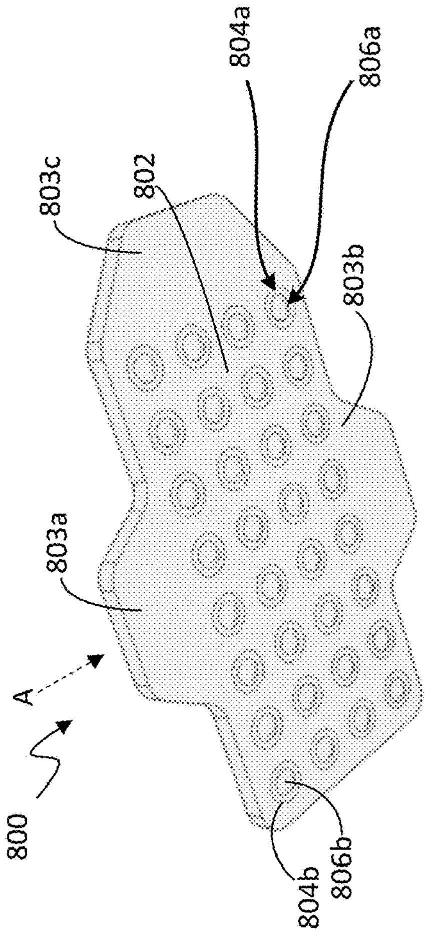

FIG. 8A is a perspective view of a bottom surface 802 of a bottom part 800 of a device after electrode structures have been encapsulated with a first flexible encapsulant to form the bottom part 800 of the device in the step 704, according to an embodiment of the system described herein. The bottom surface 802 includes the bottom surfaces of a plurality of electrode structures, for example, bottom surface 804*a*, 804*b* of electrode carriers of electrode structures and surfaces 806*a*, 806*b* of electrode protrusions (e.g., a hemispherical protrusions) of the electrode structures, which protrude from the bottom surface 802 of the bottom part 800. The plurality of bottom surfaces of electrode structures illustrated may form a continuous bottom surface 802 in combination with a bottom surface of the flexible encapsulant that occupies the remainder of the bottom surface 802 not consumed by the bottom surfaces of the electrode structures.

The step 704 also may result in the top ends of the electrodes of the electrode structures remaining exposed, extending beyond a top surface of the first flexible encapsulant; i.e., beyond a top surface of the bottom part of the device, so that the electrodes may be coupled to a configured FEC as described in more detail elsewhere herein. For example, FIG. 8B is a perspective view of a top surface 810 of the bottom part 800 of the device, according to an embodiment of the system described herein, which shows the top ends of electrodes (e.g., electrode tops 812*a,b*) extending beyond the top surface 810.

The bottom part 800 also may include portions 803*a-c* for accommodating components other than a configured FEC, and the mold used to produce the bottom part may be configured accordingly. It should be appreciated that the shape of the bottom part 800, the pattern of electrode structures, the numbers of rows (if any) and columns (if any)

of electrode structures, and the overall number of electrode structures, may be different than as illustrated in FIGS. 8A and 8B.

Figure 8C:
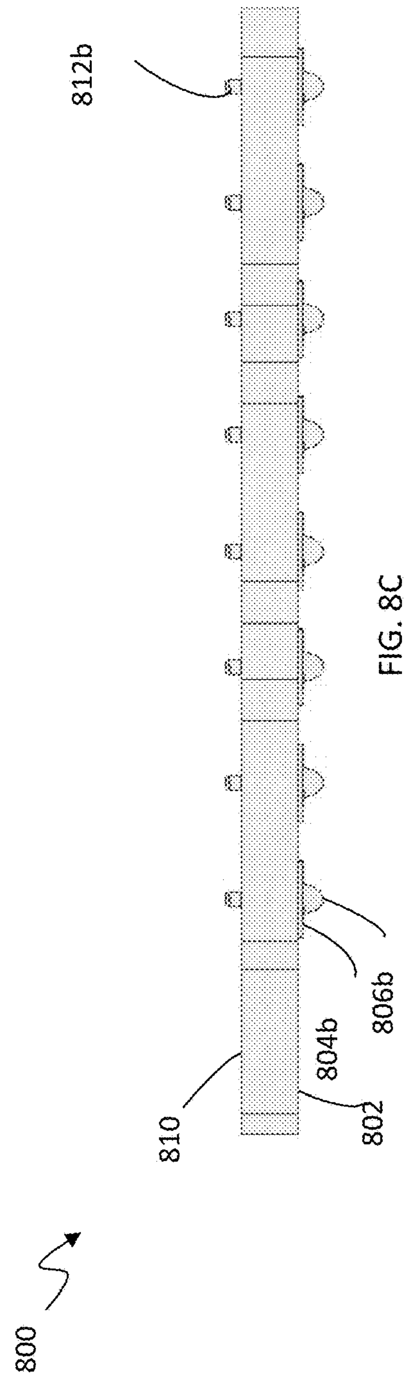

FIG. 8C is a side view of the bottom part 800 from the perspective of the arrowed, dashed line A in FIGS. 8A and 8B. As can be seen in FIG. 8C, the surfaces of the electrode protrusions (e.g., 806*b*) extend beyond the remainder of the bottom surface 802 of the bottom part 800, and the top ends of electrodes (e.g., electrode top 812*b*) extend beyond the top surface 810.

In a step 706, a configured FEC (e.g., the configured FEC 320) may be positioned above the bottom part of the device, and may be electrically coupled to the electrode structures in a step 708. For example, the tops of the electrodes (e.g., the electrodes 100) of the electrode structures may be soldered to contacts (e.g., the contacts 302*a-i*) of the configured FEC. Components other than the configured FEC also may be positioned above the bottom part of the device. These components may include one or more of the components of the electronic system 600 and other components, including, for example, interfaces for wired and/or wireless communication and interfaces for supplying power.

Figure 8E:
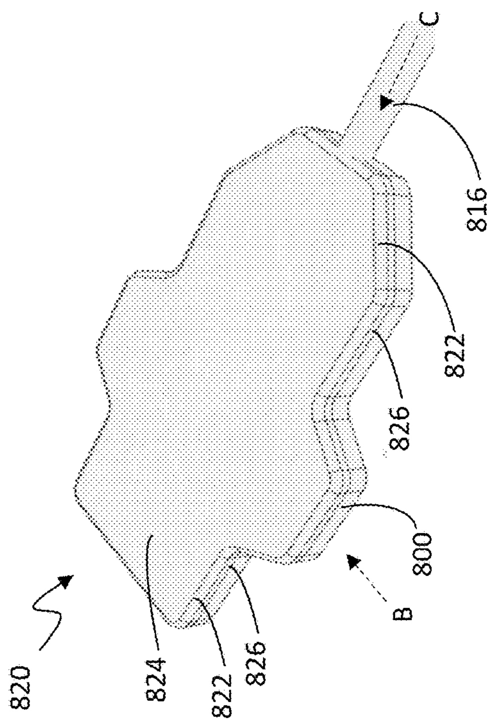
Figure 8D:
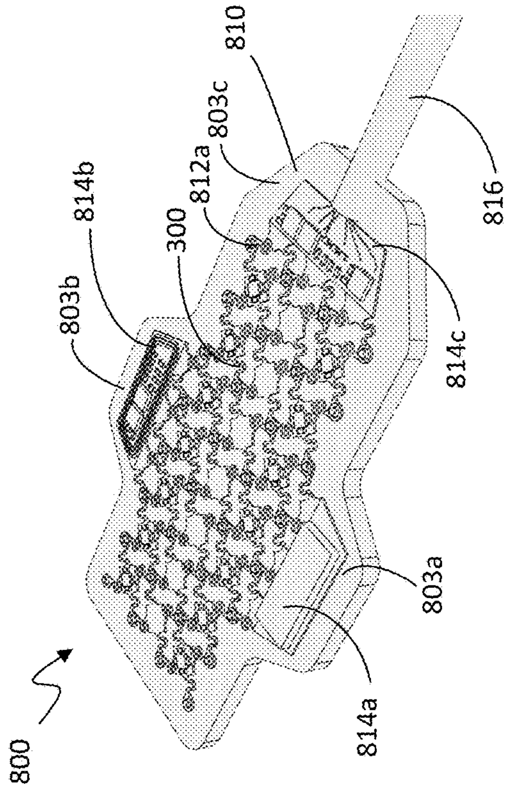

FIG. 8D is a perspective view of a top side of the bottom part 800 after the configured FEC has been electrically coupled to the electrode structures in the step 708, according to an embodiment of the system described herein. The configured FEC 320 overlays the top surface 810 of the bottom part 800 and may be electrically coupled (e.g., soldered) to the electrode structures, including the electrode top 812 of an electrode structure. In addition, electronic components 814*a-c* may overlay portions 803*a-c*, and a conduit 816 (e.g., for electric coupling) may overlay an end of the bottom part.

In a step 710, a mesh fabric (e.g., the mesh fabric 400) may be overlayed on top of the configured FEC, and the configured FEC and overlayed mesh fabric may be positioned in a second mold in a step 712. In a step 714, the configured FEC and overlayed mesh fabric may be encapsulated with a second flexible encapsulant to produce the top part of the device. The first encapsulant may consist of the same material or essentially the same material as the first flexible encapsulant.

In a step 716, the top part may be bonded to the bottom part to produce the encapsulated device. For example, as part of a molding process that produces the top part, the first and/or second encapsulants may be heated to a sufficient temperature, brought into contact with each other and then allowed to cure as one integral form. In other embodiments, a bonding agent may be applied between the top part of the bottom part to permanently bond the parts together. The encapsulated device may provide a hermetic and waterproof seal of its contents, e.g., a configured FEC, mesh fabric, electrode structures and other components, except for electrode protrusions (e.g., the electrode protrusions 806) on the bottom surface of the device (e.g., the bottom surface 802) to be used to depress into the skin of a subject to detect biopotentials therefrom.

Note that, alternatively, the REC 320', which is described elsewhere herein, may be used in places of the combination of the FEC 320 and the mesh 400 or in place of just the mesh 400. In such a case, the step 706 would position the configured REC and the steps 710, 712, 714, 716 may be eliminated and/or adapted to the REC 320' if the FEC 320 is not used.

FIG. 8E is a perspective view from above a device 820, after a top part 822 of the device has been bonded to the bottom part 800 of the device in the step 716, according to an embodiment of the system described herein. The perspective view shows a top surface 824 of the top part 822, which also serves as the top surface of the device 820. The top part 822 may be bonded to the bottom part 800 by a bonding agent that forms a bonding layer 826.

Figure 8F:
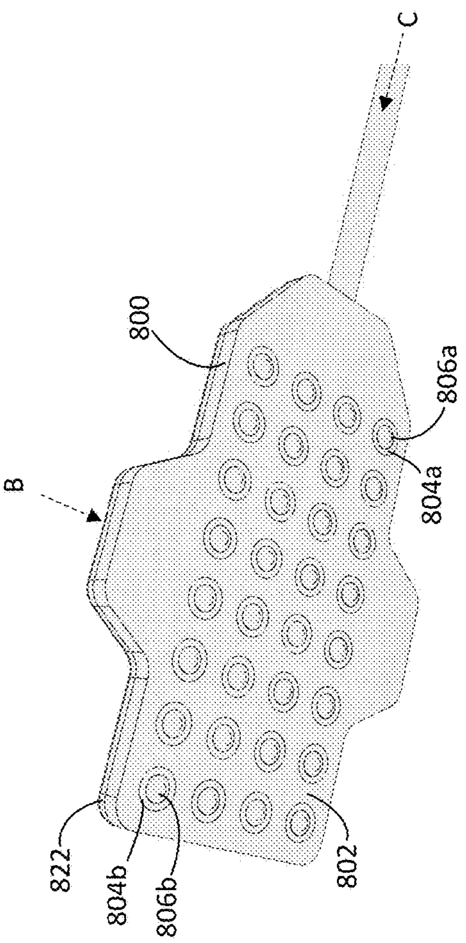
Figure 8G:
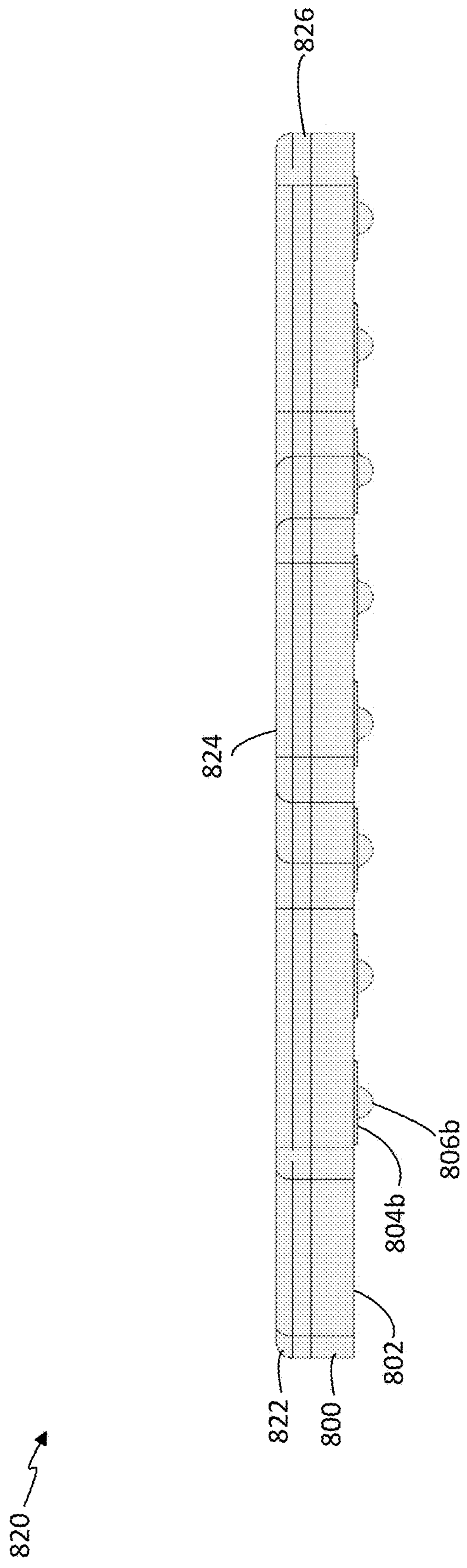
Figure 8H:
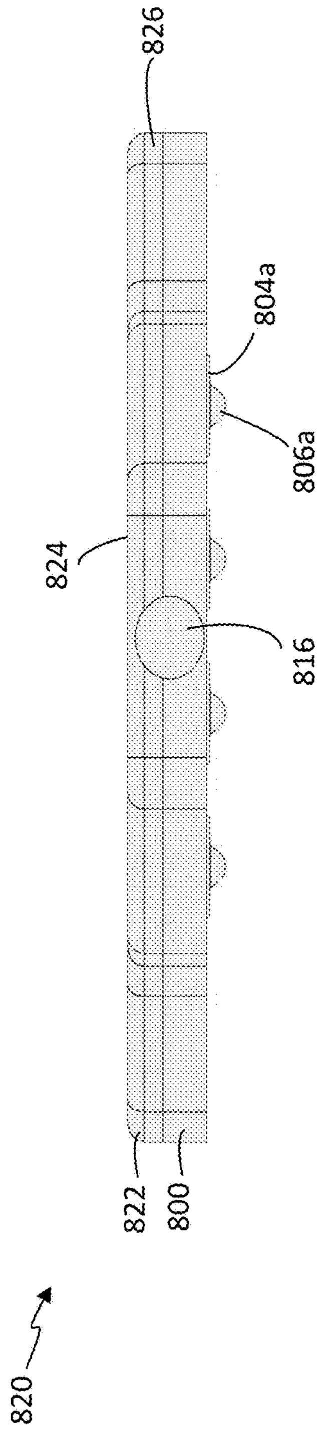

FIG. 8F is a perspective view from the underside of the device 820 according to some embodiments of the system described herein. In FIG. 8F, the bonding layer 826 is not shown. FIG. 8G is a side view of the device 820 from the perspective of the arrowed, dashed line B in FIGS. 8E and 8F. FIG. 8G is a side view of the device 820 from the perspective of the arrowed, dashed line B in FIGS. 8E and 8F. FIG. 8H is a side view of the device 820 from the perspective of the arrowed, dashed line C in FIGS. 8E and 8F. As can be seen in FIGS. 8F, 8G and 8H, the surfaces of the electrode protrusions (e.g., 806*a,b*) extend beyond the remainder of the bottom surface 802 of the bottom part 800 (which is also the bottom surface of the device 820).

In some embodiments, a skin interface may be provided that temporarily attaches an encapsulated device as described herein to the skin of a subject, for example, during operation of the encapsulated device to detect biopotentials from the subject. In some embodiments, the skin interface may be disposable in that the skin interface may be configured to be discarded after the encapsulated device is removed from skin of a subject.

Figure 9A:
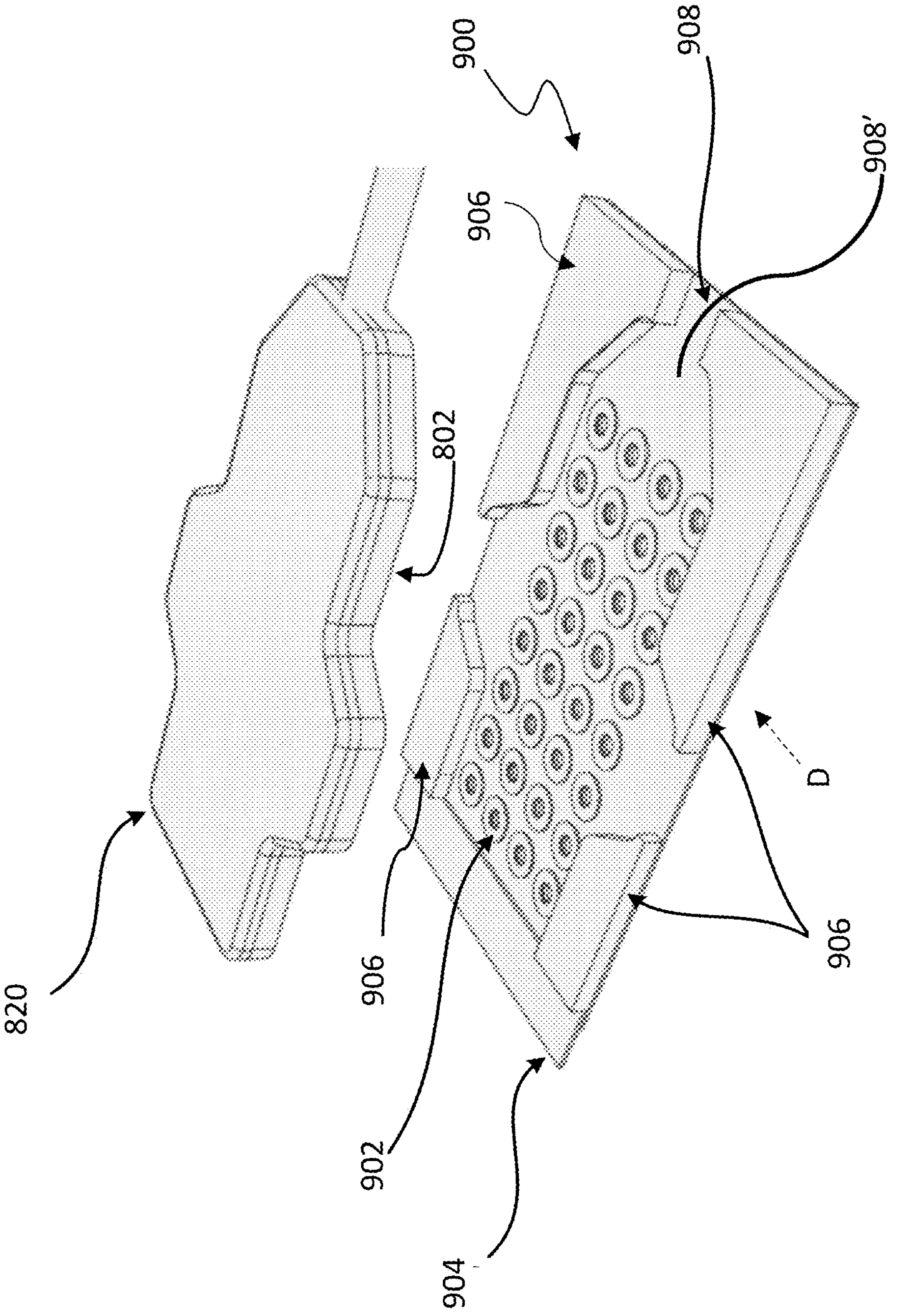
FIG. 9A illustrates a perspective view of a skin interface of a system for detecting and processing biopotentials, according to an embodiment of the system described herein.

FIG. 9A illustrates a skin interface 900 of a system for detecting and processing biopotentials, according to an embodiment of the system described herein. Other embodiments of a skin interface, for example, variations of the skin interface 900, are possible and are intended to fall within the scope of the invention. The skin interface 900 may include a substrate (e.g., silicone) 908, skin adhesive 908" (shown in FIG. 9B) configured to adhere (e.g., temporarily) to skin, and device adhesive 908' configured to adhere (e.g., temporarily) to the device 820, for example, to the flexible encapsulant of the bottom surface 802 of the device 820. The substrate 908 may be made of a silicon-based polymer.

The skin adhesive and device adhesive 908' may be thin layers coated onto either side of the substrate 908 using known techniques. The skin adhesive may be pressure sensitive and made of one or more materials optimized to adhere the substrate 908 to skin (e.g., human or animal skin). The device adhesive 908' may be made of one or more materials optimized to adhere the substrate 908 to the flexible encapsulant (e.g., silicone) used to encapsulate at least the bottom of the encapsulated device 820.

The material used as an encapsulant for at least the bottom of the encapsulated device 820 may be a material (e.g., silicone) for which it is generally difficult to adhere. Accordingly, in some embodiments, the skin interface 900 also may include a carrier layer 902 configured on a same side of the substrate 908 as the device adhesive 908' and configured to adhere to bottom surfaces (e.g., the bottom surface 802) of electrode carriers of the device 820. As illustrated in FIG. 9A, the carrier layer 902 may include several discrete sections, where each section may be shaped and sized (e.g., as an annulus) to align with a bottom surface of an electrode carrier of an electrode structure. The carrier may be made of a material to which is it generally easier to adhere (e.g., plastic) than the flexible encapsulant, and the carrier layer 902 may be made of one or more materials optimized to adhere the substrate 908 to the bottom surface of the carrier.

In some embodiments, the carrier layer 902 and the device adhesive are made of the same, or essentially the same, materials, in which case the carrier layer 902 may provide a stronger adhesion to a bottom surface of the carrier than the device adhesive 908' provides to a bottom surface of the encapsulant of the device. The device adhesive 908' may be made of the same or essentially the same materials as the skin adhesive.

The adhesives may be configured to have enough adhesive strength to remain adhered to the surface for which the layers are intended to adhere (e.g., skin, encapsulant and carrier, respectively) during use of the system for detecting and processing biopotential as described herein. In some embodiments in which the skin interface is intended to be disposable, such adhesives may be configured to be sufficiently strong enough for only a single use.

The substrate 908, skin adhesive, device adhesive 908' and carrier layer 902 each may have openings aligning to the electrode protrusions of the device 820, so that the electrode protrusions may protrude from the skin adhesive of the skin interface 900 to be pressed against the skin of a subject.

The skin interface 900 may include an alignment layer 906 on the device side of the skin interface 900 having interior sidewalls that conform to at least a portion of an exterior side perimeter of the encapsulated device 820 to assist in aligning the plurality of openings in the layers of the skin interface 900 with the plurality of electrodes of the encapsulated device 820. The alignment layer 906 may be made of foam, for example, a low durometer foam, which may be as flexible and stretchable as the substrate 908. As illustrated in FIG. 9A, the alignment layer 906 may include a plurality of discrete, separated sections, whereas other embodiments of the alignment layer 906 may be a single component that laterally surrounds the encapsulated device.

The skin interface 900 also may include a pull tab 904 configured to enable removing the skin interface from the skin and from the device (e.g., the encapsulated device 820) to which the skin interface 900 is adhered. The pull tab 904 may be affixed to one or more of the substrate 908, the skin adhesive and the device adhesive 908'. The pull tab 904 may be designed to be grippable by a human hand and of sufficient structural integrity to remain affixed to the one or more of the substrate 908, the skin adhesive and the device adhesive 908' when peeled away from the skin with sufficient force to remove the article from the skin. The pull tab 904 may be configured to not be adhesive to skin.

The skin interface 900, in particular, the geometry and materials thereof, may be configured to be at least as flexible as the encapsulated device 820 so that a system including the skin interface 906 and the encapsulated device 820 may conform to the skin of a subject.

Figure 9B:
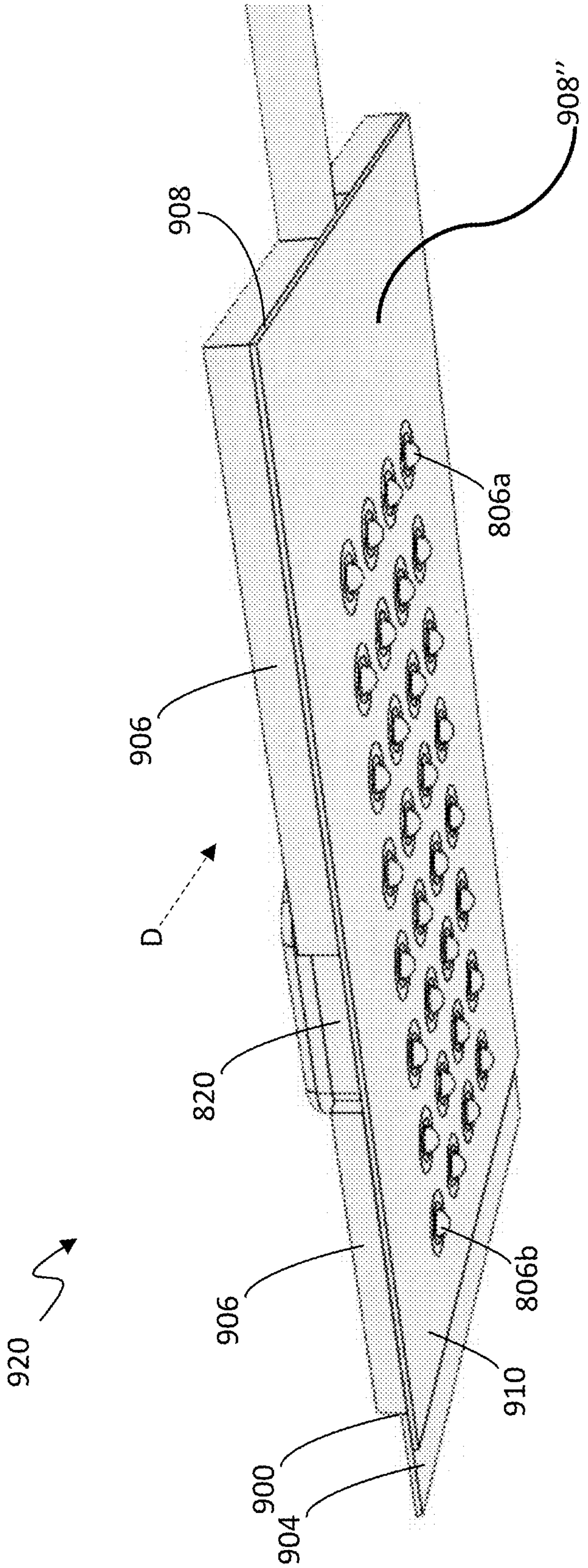
FIG. 9B illustrates a perspective view of a system for detecting and processing biopotentials, according to an embodiment of the system described herein.

FIG. 9B shows a system 920 for detecting and processing biopotentials, according to an embodiment of the system described herein. Other embodiments of a system for detecting and processing biopotentials, for example, variations of the system 920, are possible and are intended to fall within the scope of the invention.

The system 920 may include the encapsulated device 820 and the skin interface 900. The electrode protrusions of the encapsulated device, including electrode protrusions 806*a*, 806*b*, may protrude from a bottom surface 910 of the system 920. The bottom surface 910 of the system of 920 may be a bottom surface of the skin interface 900, which may include the skin adhesive 908", which may be, for example, a thin layer coated on the underside of the substrate 908. The system 920 may be adhered to the skin of a subject (e.g., a human patient or test animal) to measure biopotentials from the subject. The pressure of the skin interface 906 against the skin of the subject may trap skin moisture around the protrusions of electrodes to facilitate ionic exchange with the electrode.

It should be appreciated that, for the system 920, the number of electrodes, the number of rows and columns of electrodes, the number of electrodes per column, the number of electrodes per row and the spacing between electrodes, and thus the configuration of the FEC contacts and other components of a configured FEC, may vary, for example, depending on the intended use of the system 920, for example, an intended biological area (e.g., muscle group) of monitoring and analysis. Further, another arrangement of electrodes, and a corresponding configuration of a configured FEC, may be implemented instead of a two-dimensional array in a generally rectangular lay-out. For example, the electrodes may be arranged in one or more concentric rings of a system for detecting and processing biopotentials that has a generally circular shape. In such embodiments, the same or similar techniques described in relation to FIGS. 7-9 may be used to produce such a system. Note also that, an REC may be used in place of the FEC.

The system 920, or parts thereof, may be adhered to the skin of a subject, and biopotentials may be detected from the subject and processed by the encapsulated device.

Figure 10:
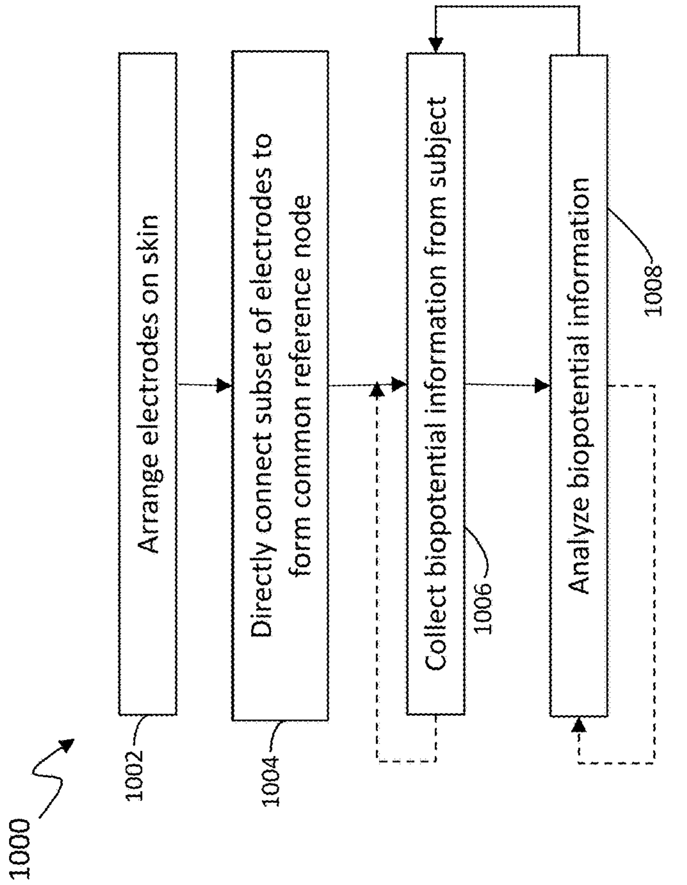
FIG. 10 is a flowchart of a method of detecting and processing biopotential signals according to an embodiment of the system described herein.

FIG. 10 is a flowchart 1000 illustrating detecting and processing biopotential signals according to an embodiment of the system described herein. Other embodiments of detecting and processing biopotential signals, for example, variations of the processing illustrated by the flowchart 1000, are possible and are intended to fall within the scope of the invention.

In a step 1002, the electrodes may be arranged on the skin of a subject, for example, as part of a system (e.g., the system 920) for detecting and processing biopotential signals described herein. In some embodiments, the system may include a skin interface (e.g., the skin interface 900) adhered to an encapsulated device (e.g., the encapsulated device 820) having electrode protrusions protruding therefrom. The skin adhesive 908" of the skin interface may be used to adhere the encapsulated device to the skin of the subject so that the electrode protrusions depress into the skin. In some embodiments, the encapsulated device may include a plurality of electrodes arranged in a pattern (e.g., two-dimensional array) resulting in a pattern of electrode protrusions protruding from the encapsulated device. This pattern of electrode protrusions may be depressed into skin in an alignment that takes into consideration the orientation of a body part or area from which biopotentials are to be detected. For example, a two-dimensional array of electrodes may be arranged in general alignment with muscle fibers of one or more muscles (e.g., of a muscle group) of the subject.

Figure 11:
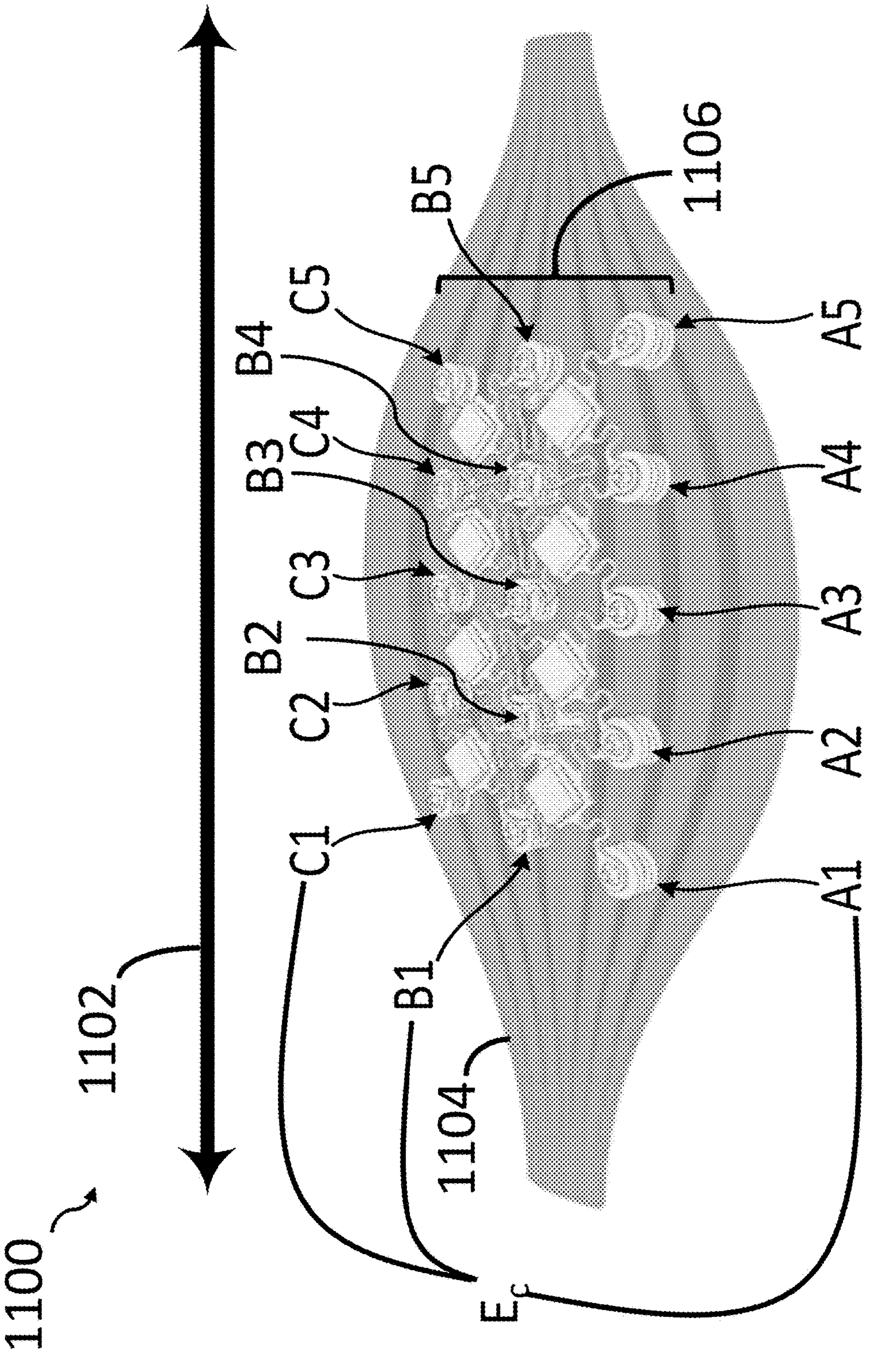
FIG. 11 is a diagram illustrating an arrangement of an electromechanical construct and electrode structures relative to a muscle, according to an embodiment of the system described herein.

FIG. 11 is a diagram illustrating an arrangement 1100 of a configured FEC 1106 electrically coupled to electrode structures, relative to a muscle 1104, according to an embodiment of the system described herein. Other embodiments of such an arrangement are possible and are intended to fall within the scope of the invention. For example, an REC may be used instead of an FEC. The configured FEC 1106 and electrode structures may be part of an encapsulate device (not shown) that is part of a system (not shown), e.g., the system 920, including a skin interface adhered to the encapsulated device and to skin (not shown) covering the muscle 1104.

The configured FEC 1106 may include a two-dimensional array of contacts, each contact electrically coupled to a respective one of the electrode structures, forming five rows of three electrical nodes: A1-A5, B1-B5 and C1-C5. That is, there are three columns A, B and C and five rows 1-5 of electrical nodes. It should be appreciated that there may be more or less columns, rows and total number of electrical nodes. Each of these electrical nodes includes an electrode of an electrode structure electrically coupled to a contact of the configured FEC 1106. Accordingly, the term "electrode" may be used interchangeably with the term "electrical node" and "node" in the context of describing aspects of the system herein in relation to FIGS. 10-12. As can be seen from FIG. 11, the columns A-C of electrodes may be generally aligned with a direction 1102 of the muscle fibers of the muscle 1104.

Returning to FIG. 10, a subset of the electrodes may be electrically coupled together to form a common reference node in a step 1004. For example, a row A1, B1 and C1 of electrodes may be electrically coupled together to form a common reference node of equipotential, which may be referred to herein as a reference node or equipotential node, $E_c$. Any combination of two or more electrodes may be coupled together to serve as the reference node, and such electrodes may be selected based on what is being observed, for example, based on the orientation of a muscle or muscle group under observation. In some embodiments, only a single electrode may serve as the reference node.

In a step 1006, biopotential information may be collected from a subject, for example, using a system (e.g., the system 920) for detecting and processing biopotentials, as described in more detail elsewhere herein. In a step 1008, the biopotential information may be analyzed, as described in more detail elsewhere herein. The biopotential information already collected may be analyzed in the step 1008 concurrently to new biopotential information being collected (e.g., in real time), as illustrated by the dashed arrowed lines in FIG. 10.

Figure 12:
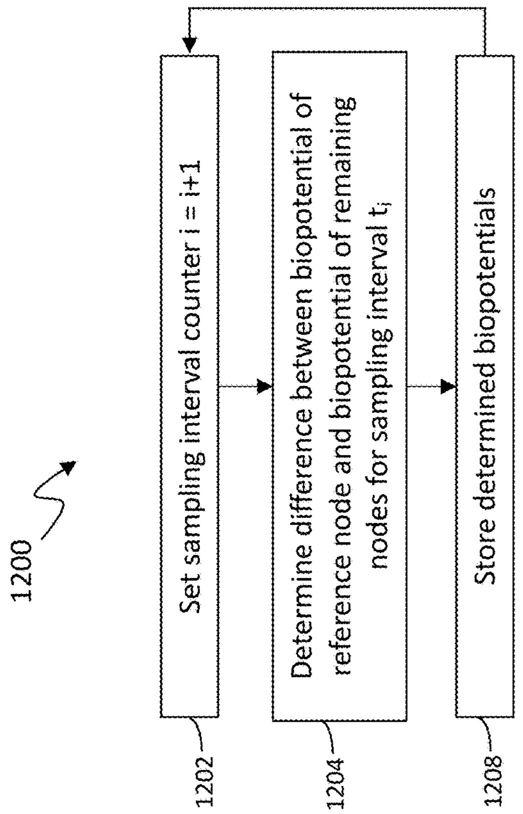
FIG. 12 is a flowchart of a method of collecting biopotential information from a subject according to an embodiment of the system described herein.

FIG. 12 is a flowchart 1200 illustrating collecting biopotential information from a subject, according to an embodiment of the system described herein. Other embodiments of collecting biopotential information from a subject, for example, variations of the processing illustrated by the flowchart 1200, are possible and are intended to fall within the scope of the invention. The processing illustrated by the flowchart 1200 may include sampling biopotential information that is being continually detected by electrodes, including the reference node and measurement electrodes. The biopotential information may be sampled for sampling intervals that are less than the measurement periods for which biopotential values will be determined, as described in more detail elsewhere herein. For example, such sampling intervals may be within a range of 50 μs to 1 ms, whereas a measurement period may be 25 ms or 50 ms, respectively.

In a step 1202, a current time interval counter i may be incremented by 1; i.e., i=i+1. In a step 1204, for each node that is not a reference node (sometimes referred to herein as "measurement nodes" or "measurement electrodes"), a difference between a biopotential of the reference node, $E_c$, detected at an instant of time within time interval $t_i$ and a biopotential of the measurement node detected at the instant of time may be determined, for example, using a circuit block 500 described in relation to FIG. 5.

For example, with reference to the circuit block 501 of the circuit 500 corresponding to the electrode A2 in FIG. 11, the control signal 510 may control the connection of the biopotential signal 512 detected from the electrode A2 to the amplifier input 534; and the control signal 506 may control no selection of either the static reference signal, $Ref_0$, or the noise cancellation reference signal, $Ref_1$. For the circuit block 501 corresponding to the electrode A2, the determined biopotential difference between A2 and $E_c$ is the difference between the output voltages 522, 524, sampled by the ADC 520. It should be appreciated that the steps 1204 may be performed concurrently, i.e., the biopotential differences determined concurrently for the measurement electrodes, for example, by different ones of the circuit blocks 501 of the circuit 500 and/or other component of the electronic system 600. For example, the ADC 520 may be configured to sample the biopotential differences for each measurement electrode at the same time, e.g., simultaneously.

In a step 1208, the biopotential differences determined in the steps 1204 may be stored, for example, in memory (e.g., non-volatile memory) found on the system (e.g., on configured FEC 320 or otherwise) and/or external to the system, as described in more detail elsewhere herein. Control may return to the step 1202 for a next sampling interval. It should be appreciated that the step 1208 may be performed concurrently for different electrodes and may be performed concurrently to the step 1204 being performed for different sampling intervals.

FIG. 13 is a flowchart 1300 illustrating processing and analyzing biopotential information collected from a subject, according to an embodiment of the system described herein. Other embodiments of processing and analyzing biopotential information collected from a subject, for example, variations of the processing illustrated by the flowchart 1300, are possible and are intended to fall within the scope of the invention.

In a step 1302, a measurement period counter, j, may be incremented. In a step 1304, for each electrode that is not part of the reference node; i.e., each measurement node (e.g., electrodes A2, A3, A4, A5, B2, B3, B4, B5, C2, C3, C4 or C5 in FIG. 11), a biopotential difference between the electrode and the reference node for the measurement period $T_j$ may be determined. For example, an RMS value of the biopotential differences between the electrode and the reference node sampled for sampling intervals within the measurement period for the measurement period $T_j$ may be determined.

A length of a measurement period may be predefined, for example, to be a value between 2.5 ms and 5 ms. The measurement periods may be considered a sliding window of time, and an RMS value for a measurement period may be calculated, where the RMS value is the RMS of the biopotential differences detected for each sampling internal within the window of time that is the measurement period. Further, each measurement period may be defined to correlate to a particular time. An RMS value that is calculated for the measurement period may be considered the magnitude of the biopotential difference for the particular time. For example, $T_j$ may correspond to a 5 millisecond unit of time, and a biopotential difference value for the 5 millisecond unit of time represented by the measurement period $T_j$ may be determined by calculating the RMS value for the biopotential differences sampled (e.g., every 50 μs) during a measurement period of time that is 2.5 milliseconds in length, spanning 1.25 milliseconds of time before and after the unit of time for which the value is being calculated.

In a step 1306, biopotential information may be stored, for example, in memory (e.g., non-volatile memory) found on the system (e.g., on configured FEC 320 or otherwise) and/or external to the system, as described in more detail elsewhere herein. The biopotential information may include the biopotential differences determined for each node for a measurement period in the step 1304. For example, the step 1306 may store the biopotential information may include the biopotential differences determined for each node for a measurement period in a data structure.

FIG. 14 is block diagram illustrating a data structure for storing biopotential information, according to embodiments of the system described herein. Other embodiments of a data structure for storing biopotential information, for example, variations of the data structure, are possible and are intended to fall within the scope of the invention. The data structure may be a biopotential table 1400.

The biopotential table 1400 may include a plurality of entries 1408, where each entry represents a node of a system for detecting and processing biopotentials, for example, one of nodes A2, A3, A4, A5, B2, B3, B4, B5, C2, C3, C4 and C5. A column 1402 is used for specifying a value (e.g., an ID) of a node represented by an entry, and each of the remaining columns 1404-1408 represents a measurement period (MP). For each entry, for each of the columns 1404-1408, the biopotential difference value determined for the period represented by the column is stored in the column. For example, the entry 1408*a* may represent a node A2 and specify: an identifier of the node A2 in the column 1402, a determined biopotential difference value for the node A2 for a measurement period $MP_1$ in the column 1404 (specifically in a cell 1404*a*); a determined biopotential difference value for the node A2 for a measurement period $MP_2$ in the column 1406; and a determined biopotential difference value for the node A2 for a measurement period $MP_n$ in the column 1408. Similarly, the entry 1408*b* may represent a node A3 and specify: an identifier of the node A3 in the column 1402, a determined biopotential difference value for the node A3 for the measurement period $MP_1$ in the column 1404 a determined biopotential difference value for the node A3 for the measurement period $MP_2$ in the column 1406 (specifically in a cell 1406*b*); and a determined biopotential difference value for the node A3 for the measurement period $MP_n$ in the column 1408. The determined biopotential difference values stored in the biopotential table 1400 may be determined as described in relation to the step 1304, described elsewhere herein.

Other information may be stored in the biopotential table 1400 including any relevant information described herein. For example, each of the entries 1408*a*-*n* may store additional information for the node represented by the entry. The biopotential table 1400 or another data structure may also store the biopotential differences determined for each node for each sampling interval, for example, to the extent it is desirable to save biopotential information at such a level of granularity and there is sufficient storage space. One or more other data structures, for example, one or more indexes, may be created from the biopotential table. Data structures other than a table may be used including, for example, an object-oriented data structure, a linked list and/or a tree.

Returning to the flowchart 1300, following performance of the step 1306, control returns to the step 1302, where the period counter is incremented, and the steps 1304 and 1306 may be repeated for the next measurement period. The measurement periods may be considered sliding windows of time, such that the one or more successive measurement periods may overlap with a current measurement period and one or more successive measurement periods may include overlapping sampling intervals.

In a step 1310, for each measurement electrode, an extent of the biopotential difference, $Vdif_x$, determined for the measurement period $T_j$ that is attributable to one or more deep muscle(s) may be determined by removing a part of the determined biopotential difference that is due to biopotential signals emanating from shallow muscles near the surface, for example, by application of Equation 1:

$$Vdif_x(deep)=Vdif_x(t_j)-Vdif_y(t_{j+n}) \quad \text{Equation 1}$$

where $Vdif_x$(deep) is the extent of the biopotential difference determined for the measurement period $T_j$ for the electrode x that attributable to one or more deep muscle(s), where $Vdif_x$ $(t_i)$ is the determined biopotential difference for the electrode x for time interval i, and where $Vdif_y$ $(t_{i+n})$ is the determined biopotential difference for the electrode y adjacent to the electrode x for time interval i+n, where n is an integer delay multiplier that is a multiple of 1 (e.g., 1, 2, 3, etc.). For example, if n=1, then $Vdif_y$ $(t_{i+n})$ is the determined biopotential difference for the electrode at a next time interval after time interval i; if i=2, then $Vdif_y$ $(t_{i+n})$ is the determined biopotential difference for the electrode two time intervals after time interval i. That is, the variable n introduces a time delay of one or more sampling intervals. Signals emanating from deep muscles are conducted through a volume of the tissue and accumulate latency as a function of distance when compared to signals originating from surface muscles. The time offset subtraction provides a mechanism for neutralizing the effect of this accumulated latency, and permitting the subtraction of the energy content from the shallow sources, the residual of which is deep signal content.

An adjacent electrode to a given electrode may be a closest electrode to the given electrode, for example, a next electrode or immediately prior electrode relative to the given electrode in a column of electrodes. For example, referring to FIG. 11, the electrode A5 may be considered adjacent to the electrode A4, and the electrode C2 may be considered adjacent to the electrode C3. Thus, for example, to determine $Vdif_x$(deep) using Equation 1 for A2 for the measurement period $T_j$ represented by column 1404 of the biopotential table 1400, the value of $Vdif_x$ $(t_j)$ for A2 may be the value stored in entry 1404*a* and the value of $Vdif_y$ $(t_{j+n})$ for A3 may be the value stored in entry 1406*b*, where column 1406 represents the time $t_{j+n}$.

The calculation reflected in the Equation 1 may be performed iteratively for several different values of n. Each resulting value, $Vdif_x$(deep), may be analyzed (e.g., compared to each other and/or other data previously detected, measured and/or calculated), to determine which amount of temporal offset for different values of n results in a most accurate determination of the extent of a biopotential difference attributable to a deep layer of muscles. For example, the different values of $Vdif_x$(deep) for each value of n for different measurement nodes may be stored, for example, in an appropriate entry of the biopotential table 1400 or in another data structure, and the values may be mathematically compared and/or or graphically depicted and visually analyzed to ascertain an optimal temporal offset value used for n. The resulting value, $Vdif_x$(deep), for the optimal temporal offset value of n may be used to represent a portion of the determined biopotential difference for the measurement node for the measurement period $T_j$ that is attributable to one or more deep muscle(s).

Other information may be determined from the determined biopotentials, and/or used to determine an optimal temporal offset for a determined biopotential. Such information may include empirical data for the muscles (e.g., of a muscle group) being observed, for example, the distance between muscles, the velocity of biopotential signals through tissue, etc.

In a step 1312, for each measurement electrode, an extent of the biopotential difference, $Vdif_x$ determined for the measurement period $t_i$ that is attributable to one or more shallow muscle(s) may be determined by removing that part of the determined biopotential difference that is due to biopotential signals emanating from deep muscles near the surface.

In some embodiments, after the performance of the step 1306 for one or more measurement periods, the steps 1310, 1312,1314 may be performed, for example, concurrently to the steps 1302, 1304,1306 being performed for other measurement periods.

Figure 15:
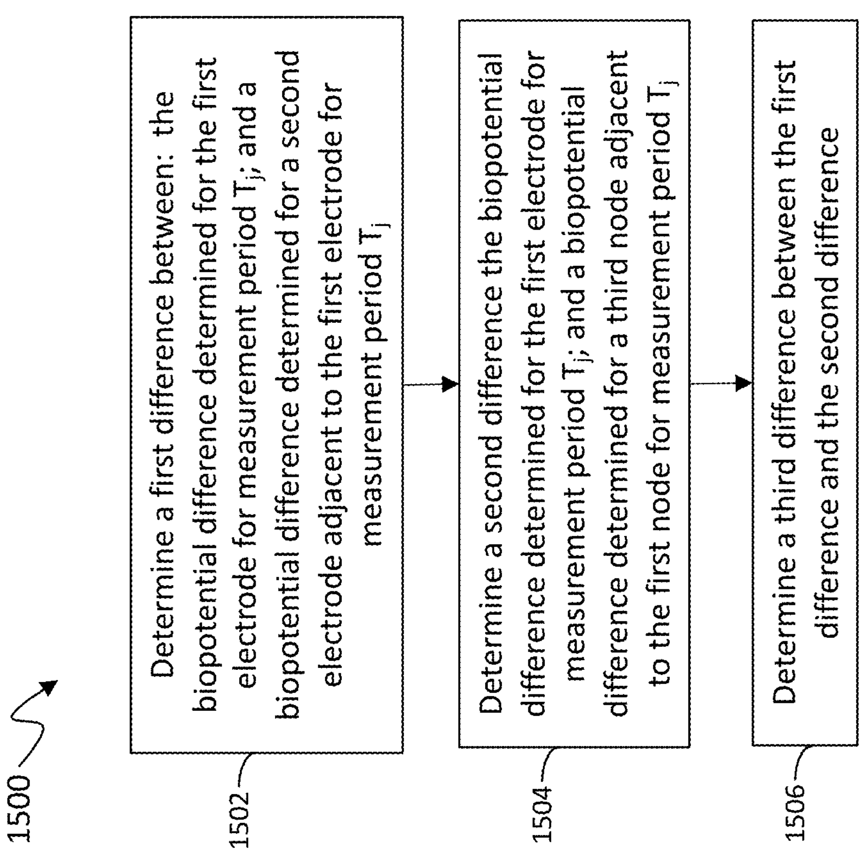
FIG. 15 is a flowchart of a method of determining an extent of a determined biopotential difference that is attributable to shallow muscles, according to an embodiment of the system described herein.

FIG. 15 is a flowchart 1500 illustrating determining an extent of a determined biopotential difference for the measurement period $t_i$ that is attributable to shallow muscles, according to an embodiment of the system described herein. Other embodiments of determining an extent of a determined biopotential difference for the measurement period $t_i$ that is attributable to shallow muscles, for example, variations of the processing illustrated by the flowchart 1500, are possible and are intended to fall within the scope of the invention.

In a step 1502, a first difference may be determined between the biopotential difference determined for a first electrode for a first measurement period and a biopotential difference determined for the first measurement period for a second electrode adjacent to the first electrode, for example, by application of Equation 2:

$$Vdif_{x1}=Vdif_x(t_j)-Vdif_y(t_j), \quad \text{Equation 2}$$

where $Vdif_x(t_j)$ is the determined biopotential difference for the electrode x for the measurement period $t_j$, where $Vdif_y(t_j)$ is the determined biopotential difference for the electrode y adjacent to the electrode x for the measurement period $t_j$, and $Vdif_{x1}$ is the first difference for the measurement period $t_j$ for the electrode x. For example, referring to FIG. 11, if the first electrode is B3, the second electrode may be B2.

In a step 1504, a second difference may be determined between the biopotential difference determined for the first electrode for the first measurement period and a biopotential determined for the first measurement period for a third electrode adjacent the first electrode, for example, by application of Equation 3:

$$Vdif_{x2}=Vdif_x(t_j)-Vdif_z(t_j), \quad \text{Equation 3}$$

where $Vdif_x(t_j)$ is the determined biopotential difference for the electrode x for the measurement period $t_j$, where $Vdif_z(t_i)$ is the determined biopotential difference for the electrode z adjacent to the electrode x for the measurement period $t_j$, and $Vdif_{x2}$ is the second difference for the measurement period $t_j$ for the electrode x. The third electrode may be on another side of the first electrode from the second electrode, e.g., in a same column. For example, referring to FIG. 11, if the first electrode is B3 and the second electrode is B2, then the third electrode may be B4.

In a step 1506, a third difference may be determined between the first difference and the second difference, for example, by application of Equation 4:

$$Vdif_{x3}=Vdif_{x1}-Vdif_{x2}, \quad \text{Equation 4}$$

where Vdifx3 is the third difference. The value of third difference may represent an extent of the determined biopotential difference for the measurement period $t_j$, $Vdif_x(t_j)$ that is attributable to one or more shallow muscles.

Any of the values determined in the steps 1502, 1504 and 1506 may be stored (e.g., on the configured FEC 320) and/or external to such system. For example, any of such values may be stored in an appropriate entry of the biopotential table 1400 or another data structure.

Various embodiments of the system described herein may be combined with each other in appropriate combinations. Additionally, in some instances, the order of steps in the flowcharts, flow diagrams and/or described flow processing may be modified, where appropriate. It should be appreciated that any of the steps described herein, including steps of the flowcharts 700, 1000, 1200, 1300, 1500, or parts thereof, may be implemented using one or more of the systems and/or data structures described in relation to FIGS. 1-6, 8A-8H, 9A, 9B and 11, or components thereof. Further, various aspects of the invention may be implemented using software, firmware, hardware, any suitable combination thereof and/or other computer-implemented modules or devices having the described features and performing the described functions. Logic that when executed performs methods described herein, steps thereof or portions of such methods or steps, may be implemented as software, firmware, hardware, or any suitable combination thereof.

Software implementations of embodiments of the system described herein may include executable code that is stored on one or more non-transitory computer-readable media and executed by one or more processors. Each of the computer-readable media may be non-transitory and include a computer hard drive, ROM, RAM, flash memory, portable computer storage media such as a CD-ROM, a DVD-ROM, a flash drive, an SD card and/or other drive with, for example, a universal serial bus (USB) interface, and/or any other appropriate tangible or non-transitory computer-readable medium or computer memory on which executable code may be stored and executed by a processor. Embodiments of the system described herein may be used in connection with any appropriate OS.

As used herein, an element or operation recited in the singular and preceded with the word "a" or "an" should be understood as not excluding plural elements or operations, unless such exclusion is explicitly recited. References to "one" embodiment or implementation of the present disclosure are not intended to be interpreted as excluding the existence of additional embodiments that also incorporate the recited features. Furthermore, a description or recitation in the general form of "at least one of [a], [b] or [c]," or equivalent thereof, should be generally construed to include [a] alone, [b] alone, [c] alone, or any combination of [a], [b] and [c]. In addition, use of a an ordinal term, e.g., "first," "second" or the like, to qualify a term for an item having multiple instances of the same name does not necessarily indicate a priority, precedence or temporal order between the instances unless otherwise indicated, but rather such ordinal terms may be used merely to distinguish between the separate instances.

Other embodiments of the system described herein will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method of determining a biopotential of deep layer muscles, comprising:

arranging a plurality of electrodes on skin of a subject in a pattern corresponding to muscle tissue fibers of the subject;

electrically coupling a first subset of the plurality of electrodes to form a common reference node having a reference potential;

determining a plurality of bipotential signal differences for each electrode of a second subset of the plurality of electrodes that are not members of the first subset, including, for each of the plurality of the second subset of electrodes, determining a biopotential difference between a biopotential detected by each electrode of the second subset of electrodes and the reference potential; and for at least one electrode of the second subset of electrodes, determining an extent of the biopotential difference attributable to at least one deep-layer muscle based on a difference between a first measured value at a first point in time of the biopotential difference at the at least one electrode and a second measured value at a second point in time different from the first point in time of a biopotential difference at an electrode of the second subset that is adjacent to the at least one electrode.

2. The method of claim 1, further comprising:

electrically coupling a third subset of the plurality of electrodes to form a global common mode potential that provides common mode noise mitigation, wherein the second subset of the plurality of electrodes is separate from the first subset of the plurality of electrodes and separate from the second subset of the plurality of electrodes.

3. The method of claim 1, wherein the pattern is a two-dimensional array having a plurality of columns of the electrodes arranged in a first dimension parallel with the muscle tissue fibers and a plurality of rows of the electrodes arranged in a second dimension orthogonal to the first dimension.

4. The method of claim 3, wherein the first subset of electrodes is one of the plurality of rows of electrodes.

5. The method of claim 1, further comprising:

storing in a first data structure, for each of the plurality of second subset of electrodes, a value indicative of the extent of the biopotential difference attributable to the at least one deep-layer muscle.

6. The method of claim 1, further comprising:

for each of the plurality of the second subset of electrodes, determining an extent of the biopotential difference attributable to at least one shallow-layer muscle based on the plurality of biopotential differences.

7. The method of claim 6, further comprising:

storing in a first data structure, for each of the plurality of the second subset of electrodes, a first value indicative of the extent of the biopotential difference attributable to the at least one deep-layer muscle and a second value indicative of the extent of the biopotential difference attributable to the at least one shallow-layer muscle.

8. The method of claim 1, wherein determining the reference potential and determining the biopotential difference for each of the second subset of electrodes includes using differential amplifier circuitry.

9. The method of claim 1, wherein the biopotential signals are triggered by motoneurons.

10. The method of claim 1, wherein multiple values are determined for the extent of the biopotential difference attributable to at least one deep-layer muscle by determining the difference between the first measured value at the first point in time of the biopotential difference at the at least one electrode and a plurality of measured values at a plurality of points in time different from the first point in time of a biopotential difference at the electrode of the second subset that is adjacent to the at least one electrode.

11. The method of claim 1, wherein each of the multiple values is analyzed to determine which of the plurality of points in time different from the first point in time result in a most accurate value for the extent of the biopotential difference attributable to at least one deep-layer muscle.

12. A non-transitory computer readable medium containing software that, when executed by a processor, determines a biopotential of deep layer muscles using a plurality of electrodes on skin of a subject in a pattern corresponding to muscle tissue fibers of the subject where a first subset of the plurality of electrodes is electrically coupled to form a common reference node having a reference potential, the software comprising:

executable code that determines a plurality of bipotential signal differences for a second subset of electrodes that are not members of the first subset, including, for each of the plurality of the second subset of electrodes, determining a biopotential difference between a biopotential detected by each of the non-member electrodes and the reference potential; and executable code that, for at least one of the second subset of electrodes, determines an extent of the biopotential difference attributable to at least one deep-layer muscle based on a difference between a first measured value at a first point in time of the biopotential difference at the at least one electrode and a second measured value at a second point in time different from the first point in time of a biopotential difference at an electrode of the second subset that is adjacent to the at least one electrode.

13. The non-transitory computer readable medium of claim 12, wherein multiple values are determined for the extent of the biopotential difference attributable to at least one deep-layer muscle by determining the difference between the first measured value at the first point in time of the biopotential difference at the at least one electrode and a plurality of measured values at a plurality of points in time different from the first point in time of a biopotential difference at the electrode of the second subset that is adjacent to the at least one electrode.

14. The non-transitory computer readable medium of claim 13, wherein each of the multiple values is analyzed to determine which of the plurality of points in time different from the first point in time result in a most accurate value for the extent of the biopotential difference attributable to at least one deep-layer muscle.

15. A device that determines a biopotential of deep layer muscles, comprising:

a plurality of electrodes that are arrangeable on skin of a subject in a pattern corresponding to muscle tissue fibers of the subject, a first subset of the plurality of electrodes being coupled to form a common reference node having a reference potential; and a digital signal processor that receives signals from the plurality of electrodes and determines a plurality of bipotential signal differences for a second subset of electrodes of the plurality of electrodes that are not members of the first subset, including, for each of the plurality of the second subset of electrodes, determining a biopotential difference between a biopotential detected by each of the second subset of electrodes and the reference potential and, for each of the second subset of electrodes, determines an extent of the biopotential difference attributable to at least one deep-layer muscle based on a difference between a first measured value at a first point in time of the biopotential difference at the at least one electrode and a second measured value at a second point in time different from the first point in time of a biopotential difference at an electrode of the second subset that is adjacent to the at least one electrode.

16. The device of claim 15, wherein the device is part of a system for detecting and processing biopotential signals.

17. The device of claim 15, wherein multiple values are determined for the extent of the biopotential difference attributable to at least one deep-layer muscle by determining the difference between the first measured value at the first point in time of the biopotential difference at the at least one electrode and a plurality of measured values at a plurality of points in time different from the first point in time of a biopotential difference at the electrode of the second subset that is adjacent to the at least one electrode.

18. The device of claim 17, wherein each of the multiple values is analyzed to determine which of the plurality of points in time different from the first point in time result in a most accurate value for the extent of the biopotential difference attributable to at least one deep-layer muscle.

* * * * *